United States Patent
Mansky et al.

(10) Patent No.: US 6,878,344 B2
(45) Date of Patent: Apr. 12, 2005

(54) APPARATUS FOR TESTING COMPOSITIONS IN CONTACT WITH A POROUS MEDIUM

(75) Inventors: Paul Mansky, San Francisco, CA (US); Richard Tiede, San Jose, CA (US); Steve Havadtoy, Lauderdale By The Sea, FL (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/116,805

(22) Filed: Apr. 5, 2002

(65) Prior Publication Data

US 2002/0110925 A1 Aug. 15, 2002

Related U.S. Application Data

(62) Division of application No. 09/593,730, filed on Jun. 13, 2000, now Pat. No. 6,455,007.

(51) Int. Cl.[7] .................................................. G01N 1/28
(52) U.S. Cl. .................. 422/101; 422/99; 422/102; 435/288.4; 435/288.5; 435/297.1; 436/177; 436/178; 436/180
(58) Field of Search ................................ 422/100, 101, 422/130, 61, 942, 946, 947, 948, 104, 58, 99, 102; 436/177, 178, 180; 435/287.1, 297.1, 297.5, 288.4, 288.5

(56) References Cited

U.S. PATENT DOCUMENTS

| | | | |
|---|---|---|---|
| 2,568,707 A | | 9/1951 | Bernstein |
| 3,378,481 A | * | 4/1968 | Saravis et al. |
| 3,390,962 A | * | 7/1968 | Goldsmith .................... 422/58 |
| 3,888,770 A | * | 6/1975 | Avital et al. ................. 210/238 |
| 4,087,327 A | * | 5/1978 | Feder et al. .............. 435/297.2 |
| 4,219,530 A | * | 8/1980 | Kopp et al. .................... 422/69 |
| 4,232,076 A | * | 11/1980 | Stetson et al. ................. 156/79 |

(Continued)

FOREIGN PATENT DOCUMENTS

| | | |
|---|---|---|
| DE | 41 14 611 A1 | 11/1991 |
| EP | 0 098 534 A1 * | 1/1984 |
| EP | 0 272 043 | 6/1988 |
| GB | 624054 | 5/1947 |
| GB | 2 237 243 A * | 1/1991 |
| WO | WO 98/30898 * | 7/1998 |
| WO | 99/34011 | 7/1999 |
| WO | 00/24511 | 5/2000 |
| WO | 01/19502 | 3/2001 |

*Primary Examiner*—Lyle A. Alexander

(57) ABSTRACT

An apparatus for use in testing a plurality of compositions in parallel. The apparatus includes an upper plate having a plurality of openings extending therethrough to form upper fluid chambers and a lower plate having a plurality of openings extending at least partially therethrough to form cavities. A central plate having a plurality of openings extending therethrough to form central fluid chambers is positioned between the upper and lower plates with the central chambers in alignment with the upper chambers and the cavities. A porous sheet is interposed between the upper and central plates such that an upper surface of the sheet is in contact with fluid within the upper chamber and a lower surface of the sheet is in contact with fluid within the central chamber. The apparatus further includes a flexible membrane positioned between the lower and central plates such that changes in pressure within the cavities or fluid chambers cause deflection of the membrane to force fluid to pass through the porous sheet.

26 Claims, 21 Drawing Sheets

U.S. PATENT DOCUMENTS

| | | | | |
|---|---|---|---|---|
| 4,288,228 A | * | 9/1981 | Oberhardt | 422/56 |
| 4,304,865 A | * | 12/1981 | O'Brien et al. | 435/401 |
| 4,493,815 A | * | 1/1985 | Fernwood et al. | 422/101 |
| 4,526,690 A | * | 7/1985 | Kiovsky et al. | 210/321.84 |
| 4,661,455 A | * | 4/1987 | Hubbard | 435/297.1 |
| 4,661,458 A | * | 4/1987 | Berry et al. | 210/321.75 |
| 4,734,192 A | * | 3/1988 | Champion et al. | 210/321.72 |
| 4,770,856 A | * | 9/1988 | Uthemann et al. | 422/104 |
| 4,777,021 A | * | 10/1988 | Wertz et al. | 422/101 |
| 4,787,988 A | * | 11/1988 | Bertoncini et al. | 210/808 |
| 4,818,701 A | * | 4/1989 | Littlehales | 422/101 |
| 4,828,801 A | * | 5/1989 | Lombardy wife Alric et al. | 422/101 |
| 4,839,280 A | * | 6/1989 | Banes | 428/447 |
| 4,879,431 A | * | 11/1989 | Bertoncini | 141/244 |
| 4,895,706 A | * | 1/1990 | Root et al. | 422/102 |
| 4,912,057 A | * | 3/1990 | Guirguis et al. | 435/288.4 |
| 5,039,493 A | * | 8/1991 | Oprandy | 422/101 |
| 5,047,215 A | * | 9/1991 | Manns | 210/473 |
| 5,108,603 A | * | 4/1992 | Schuette | 210/321.72 |
| 5,141,719 A | * | 8/1992 | Fernwood et al. | 422/101 |
| 5,188,733 A | * | 2/1993 | Wang et al. | 210/321.84 |
| 5,210,021 A | * | 5/1993 | Goodwin, Jr. | 435/287.1 |
| 5,227,137 A | * | 7/1993 | Monti et al. | 422/101 |
| 5,248,753 A | * | 9/1993 | Pedretti et al. | 528/176 |
| 5,284,753 A | | 2/1994 | Goodwin, Jr. | 435/30 |
| 5,324,483 A | * | 6/1994 | Cody et al. | 422/101 |
| 5,342,581 A | * | 8/1994 | Sanadi | 422/101 |
| 5,348,884 A | * | 9/1994 | Kulla | 435/287.7 |
| 5,459,069 A | * | 10/1995 | Palsson et al. | 435/289.1 |
| 5,576,211 A | * | 11/1996 | Falkenberg et al. | 435/297.1 |
| 5,578,275 A | * | 11/1996 | Rosenberg et al. | 149/109.6 |
| 5,693,537 A | * | 12/1997 | Wilson et al. | 435/297.5 |
| 5,770,157 A | * | 6/1998 | Cargill et al. | 422/101 |
| 5,922,591 A | * | 7/1999 | Anderson et al. | 422/100 |
| 5,961,926 A | * | 10/1999 | Kolb et al. | 422/101 |
| 6,008,049 A | * | 12/1999 | Naughton et al. | 435/1.1 |
| 6,022,742 A | * | 2/2000 | Kopf | 210/791 |
| 6,037,171 A | * | 3/2000 | Larsson | 435/174 |
| 6,054,100 A | * | 4/2000 | Stanchfield et al. | 422/101 |
| 6,066,496 A | * | 5/2000 | Bridges | 435/297.1 |
| 6,159,368 A | * | 12/2000 | Moring et al. | 210/258 |
| 6,194,160 B1 | * | 2/2001 | Levin | 422/101 |
| 6,197,595 B1 | * | 3/2001 | Anderson et al. | 422/100 |
| 6,218,182 B1 | * | 4/2001 | Naughton et al. | 435/1.1 |
| 6,228,607 B1 | * | 5/2001 | Kersten et al. | 435/284.1 |
| 6,303,389 B1 | * | 10/2001 | Levin et al. | 422/101 |
| 6,309,889 B1 | * | 10/2001 | Cutler et al. | 422/102 |
| 6,326,211 B1 | * | 12/2001 | Anderson et al. | 422/101 |
| 6,349,588 B1 | * | 2/2002 | Brown et al. | 73/150 A |
| 6,350,414 B1 | * | 2/2002 | Ballin et al. | 422/101 |
| 6,406,605 B1 | * | 6/2002 | Moles | 137/833 |
| 6,479,300 B1 | * | 11/2002 | Jiang et al. | 436/518 |

* cited by examiner

TABLE I

ALL VALUES ARE GIVEN IN PARTS PER MILLION (ppm) BY MASS

| ROW | INGREDIENT | COLUMN 1 | 2 | 3 | 4 | 5 | 6 | 7 | 8 | 9 | 10 | 11 | 12 |
|---|---|---|---|---|---|---|---|---|---|---|---|---|---|
| 1 | PVP | 0 | 9 | 18 | 27 | 36 | 45 | 55 | 64 | 73 | 82 | 91 | 100 |
| 2 | PVP-NO | 0 | 9 | 18 | 27 | 36 | 45 | 55 | 64 | 73 | 82 | 91 | 100 |
| 3 | SWE | 0 | 9 | 18 | 27 | 36 | 45 | 55 | 64 | 73 | 82 | 91 | 100 |
| 4 | SDS | 0 | 91 | 182 | 273 | 364 | 455 | 545 | 636 | 727 | 818 | 909 | 1000 |
| 5 | PVP | 100 | 100 | 100 | 100 | 100 | 100 | 100 | 100 | 100 | 100 | 100 | 100 |
| 5 | SDS | 0 | 91 | 182 | 273 | 364 | 455 | 545 | 636 | 727 | 818 | 909 | 1000 |
| 6 | PVP-NO | 100 | 100 | 100 | 100 | 100 | 100 | 100 | 100 | 100 | 100 | 100 | 100 |
| 6 | SDS | 0 | 91 | 182 | 273 | 364 | 455 | 545 | 636 | 727 | 818 | 909 | 1000 |
| 7 | SWE | 100 | 100 | 100 | 100 | 100 | 100 | 100 | 100 | 100 | 100 | 100 | 100 |
| 7 | SDS | 0 | 91 | 182 | 273 | 364 | 455 | 545 | 636 | 727 | 818 | 909 | 1000 |
| 8 | PVP | 0 | 9 | 18 | 27 | 36 | 45 | 55 | 64 | 73 | 82 | 91 | 100 |
| 8 | SWE | 100 | 91 | 82 | 73 | 64 | 55 | 45 | 36 | 27 | 18 | 9 | 0 |

FIG.12

TABLE II

| RED | 218 | 219 | 222 | 223 | 221 | 220 | 222 | 223 | 225 | 225 | 226 |
|---|---|---|---|---|---|---|---|---|---|---|---|
| | 223 | 220 | 221 | 222 | 221 | 221 | 224 | 221 | 219 | 219 | 220 |
| | 219 | 219 | 221 | 219 | 219 | 219 | 220 | 219 | 221 | 221 | 223 |
| | 218 | 218 | 216 | 224 | 219 | 222 | 223 | 221 | 220 | 220 | 221 |
| | 227 | 220 | 224 | 225 | 223 | 223 | 224 | 223 | 220 | 220 | 220 |
| | 223 | 222 | 224 | 222 | 228 | 224 | 221 | 221 | 220 | 221 | 220 |
| | 221 | 221 | 224 | 221 | 219 | 222 | 222 | 221 | 221 | 223 | 221 |
| | 220 | 224 | 222 | 223 | 222 | 221 | 221 | 222 | 220 | 220 | 226 |
| GREEN | 162 | 180 | 194 | 200 | 198 | 204 | 205 | 207 | 208 | 209 | 210 |
| | 206 | 212 | 213 | 215 | 215 | 215 | 217 | 219 | 218 | 218 | |
| | 181 | 185 | 195 | 197 | 195 | 195 | 196 | 200 | 205 | 204 | 220 |
| | 141 | 140 | 141 | 143 | 139 | 136 | 135 | 131 | 132 | 131 | 207 |
| | 212 | 210 | 207 | 210 | 206 | 206 | 205 | 200 | 196 | 193 | 124 |
| | 223 | 222 | 222 | 222 | 221 | 213 | 214 | 213 | 211 | 210 | 178 |
| | 201 | 180 | 200 | 188 | 176 | 147 | 131 | 131 | 131 | 131 | 204 |
| | 203 | 201 | 198 | 197 | 192 | 182 | 180 | 183 | 188 | 202 | 125 |
| | | | | | | | | | | | 208 |
| BLUE | 186 | 196 | 204 | 208 | 206 | 210 | 211 | 213 | 214 | 215 | 216 |
| | 212 | 213 | 216 | 218 | 218 | 218 | 219 | 220 | 218 | 218 | 220 |
| | 196 | 198 | 206 | 205 | 204 | 200 | 205 | 203 | 211 | 209 | 213 |
| | 172 | 170 | 168 | 176 | 175 | 167 | 166 | 163 | 163 | 162 | 153 |
| | 217 | 214 | 212 | 216 | 212 | 212 | 212 | 209 | 211 | 203 | 194 |
| | 220 | 222 | 221 | 222 | 224 | 216 | 217 | 216 | 205 | 214 | 210 |
| | 209 | 195 | 209 | 200 | 196 | 179 | 163 | 163 | 164 | 163 | 159 |
| | 209 | 209 | 207 | 207 | 203 | 195 | 195 | 197 | 201 | 209 | 214 |

FIG. 14

APPARATUS FOR TESTING COMPOSITIONS IN CONTACT WITH A POROUS MEDIUM

This is a Division of application No. 09/593,730, filed Jun. 13, 2000, now U.S. Pat. No. 6,455,007.

BACKGROUND OF THE INVENTION

The present invention relates generally to apparatus and methods for testing a plurality of compositions in parallel, and more particularly, to apparatus and methods for testing compositions in contact with a porous medium.

Testing of chemical formulations often involves exposing the chemicals to a porous material such as a fabric which absorbs or interacts with the chemicals. Developers of fabric care products, for example, test different chemical compositions and formulations by exposing pieces of fabric to the compositions or formulations, and measuring the effects on the fabric's appearance, physical, or chemical properties which result. The types of chemicals or compositions tested in this way may include surfactants, polymers, dyes, bleaches, perfumes, buffers, electrolytes, builders (e.g., calcium sequestering agents), flame retarding agents, and others. Some of the benefits which may be desirable to deliver with such compositions, and which are therefore desirable to measure after exposing the fabric to the compositions or formulations, include release or removal of soils and stains, dye retention by a fabric during washing, prevention of dye transfer from one fabric to another, prevention of soil redeposition, resistance to the abrasion which occurs due to fabrics rubbing against each other during washing, building up of fibers to increase the life of a garment, reduction or prevention of wrinkles, reduction or prevention of static buildup, and improvement or preservation of the feel or texture of a fabric.

Currently used methods of testing for such benefits are extremely laborious, and limit the rate at which new compositions and formulations can be tested. The slowest testing methods involve washing fabrics in conventional full sized washing machines, or doing hand washing in a basin. Some degree of miniaturization has been introduced through the use of instruments such as the Washtec Linitester (manufactured by Roaches) or the Turgotometer (manufactured by Heraeus). In these instruments, washing is done in vessels of reduced volume, typically 0.5–2 liters, and multiple vessels are tested simultaneously. For example, the Heraeus Turgotometer consists of six one liter pots arranged in a straight line, each with an overhead stirrer to provide agitation similar to that found in top-loading washing machines. In the Roaches Washtec, up to twelve 1 liter vessels are mounted radially on a central axel, which is rotated to give an end-over-end tumbling motion and provide agitation. In both cases, the temperature is controlled through a thermostatted bath which surrounds the vessels.

Although these instruments represent a significant improvement over testing methods which utilize full scale washing apparatus, they still require a tremendous amount of manual labor, take up a great deal of space, and have limited throughput. Detergent formulations are extremely complex, often consisting of ten or more ingredients. While significant improvements in detergent performance can be and have been attained by introducing new ingredients or changing formulations, the size of the parameter space to be tested is enormous, including variables related to both chemical structure and formulations. It is therefore, desirable to develop methods and apparatus which allow high-throughput testing of compositions and formulations for fabric care. Ideally, it is desirable to obtain high throughput and miniaturization without sacrificing relevance of the results to more realistic conditions.

One possible method of high throughput testing of fabric care compositions and formulations is to place small, individual pieces of fabric in an array of small vessels, e.g. in a microtiter plate. One drawback to this method is that the individual pieces of fabric are difficult to handle and must be left in the wells during subsequent, handling, treatment, and analysis. If the pieces of fabric are removed from the wells, special handling equipment is required. Also, each piece of fabric may need to be individually labeled to prevent misidentification of the composition used to soak the fabric. Furthermore, it is difficult to simulate the agitation of fabric within a washing machine since the fabric is simply soaking in the fluid.

There is, therefore, a need for an apparatus and method for testing compositions in parallel with a continuous sheet of material having a plurality of porous test regions, which can be easily analyzed upon completion of testing. There is also a need for an apparatus and method for forcing fluid through the porous material or in contact with the material to simulate agitation of the porous material within the fluid.

SUMMARY OF THE INVENTION

An apparatus and method for testing compositions in contact with a porous medium are disclosed. The apparatus and method improve the productivity in testing variations of compounds by permitting large numbers of compositions to be tested simultaneously (in "parallel"), in an efficient manner that is amenable to various forms of automation to provide high-throughput.

An apparatus for use in testing a plurality of compositions in parallel generally comprises a first plate, a second plate, and a sheet having porous test regions interposed therebetween. The second plate has a plurality of openings extending therethrough to form a plurality of fluid chambers. The test regions are separated by a seal integral with the sheet to prevent fluid transfer between the test regions. The test regions are aligned with the fluid chambers such that each of the chambers is in contact with one of the test regions.

In another aspect of the invention an apparatus for use in performing a plurality of tests in parallel generally comprises a first plate having a plurality of openings extending at least partially therethrough to form fluid chambers and a second plate having a plurality of openings extending at least partially therethrough to form cavities. A sheet having porous test regions is interposed between the first and second plates such that at least a portion of a first surface of the sheet is exposed to the fluid chambers and at least a portion of a second surface of the sheet is exposed to the cavities. The apparatus further includes a flexible membrane positioned between the first and second plates such that changes in pressure within the cavities cause deflection of the membrane away from the sheet to force fluids to pass through the porous test regions.

In another aspect of the invention an apparatus for use in performing a plurality of tests in parallel generally comprises a first plate having openings extending at least partially therethrough to form a plurality of fluid chambers and a second plate having openings extending at least partially therethrough to form a plurality of cavities. A sheet having porous test regions is interposed between the first and second plates such that a first surface of the sheet is at least partially exposed to the fluid chambers. A flexible membrane is positioned between the first and second plates such that changes in pressure within the fluid chambers or cavities cause deflection of the membrane and forces fluid through the porous test region.

In another aspect of the invention, an apparatus for use in performing a plurality of tests in parallel generally comprises a first plate having openings extending at least partially therethrough to form a plurality of fluid chambers and a second plate having openings extending at least partially therethrough to form a plurality of cavities. A flexible membrane is interposed between the first and second plates such that changes in pressure within the cavities cause deflection of the membrane to change pressure within the fluid chamber. The apparatus further comprises a plurality of test materials having different compositions. The plurality of test materials are disposed for fluid communication with the plurality of cavities.

A method for contacting fluid with a porous medium generally comprises supplying a fluid to a plurality of fluid chambers in a test apparatus. The test apparatus generally comprises a first plate defining a plurality of fluid chambers and second plate defining a plurality of cavities aligned with the plurality of fluid chambers. A test sheet is interposed between the first plate and the second plate such that a surface of the test sheet is at least partially exposed to the plurality of fluid chambers. The test sheet includes a plurality of porous test regions aligned with the plurality of fluid chambers. A flexible membrane is interposed between the test sheet and the second plate such that a surface of the flexible membrane is at least partially exposed to the cavities. The method further includes changing pressure within at least one of the plurality of fluid chambers and the plurality of cavities to move the flexible membrane relative to the plurality of chambers or cavities, such that the fluid contacts the plurality of test regions.

In yet another aspect of the invention, an apparatus for use in performing a plurality of tests in parallel generally includes an upper plate having a plurality of openings extending therethrough to form upper fluid chambers and a lower plate having a plurality of openings extending at least partially therethrough to form cavities. A central plate having a plurality of openings extending therethrough to form central fluid chambers is positioned between the upper and lower plates with the central chambers in alignment with the upper chambers and the cavities. A sheet having porous test regions is interposed between the upper and central plates such that an upper surface of the sheet is exposed to the upper chamber and a lower surface of the sheet is exposed to the central chamber. The apparatus further includes a flexible membrane interposed between the lower and central plates such that changes in pressure within the cavities cause deflection of the membrane to force fluid to pass through the porous test regions.

A method of flowing fluid through a porous medium in the apparatus generally comprises changing pressure within the fluid chambers or cavities to move the flexible membrane relative to the porous medium and force fluid therethrough.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

FIG. 12 is a table (Table I) listing a library of different test fluids for an experiment described below in Example 3.

FIG. 14 is a table (Table II) listing red-green-blue spectrum analysis coordinates from the test regions of the test sheet shown in FIG. 13A.

Corresponding reference characters indicate corresponding parts throughout the several views of the drawings.

DETAILED DESCRIPTION OF THE INVENTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1A:
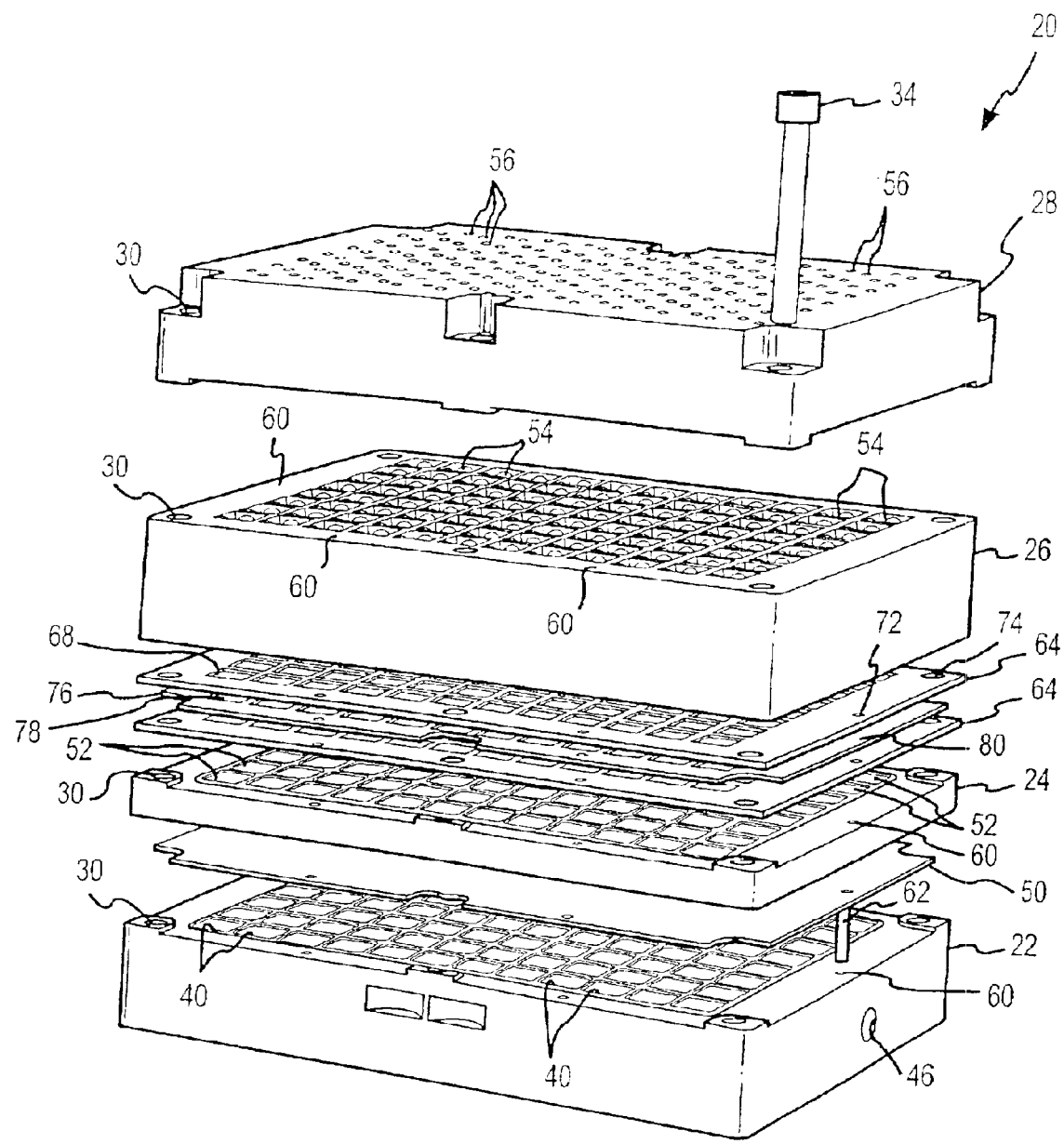
FIG. 1A is an exploded perspective of one embodiment of an apparatus of the present invention.
Figure 1B:
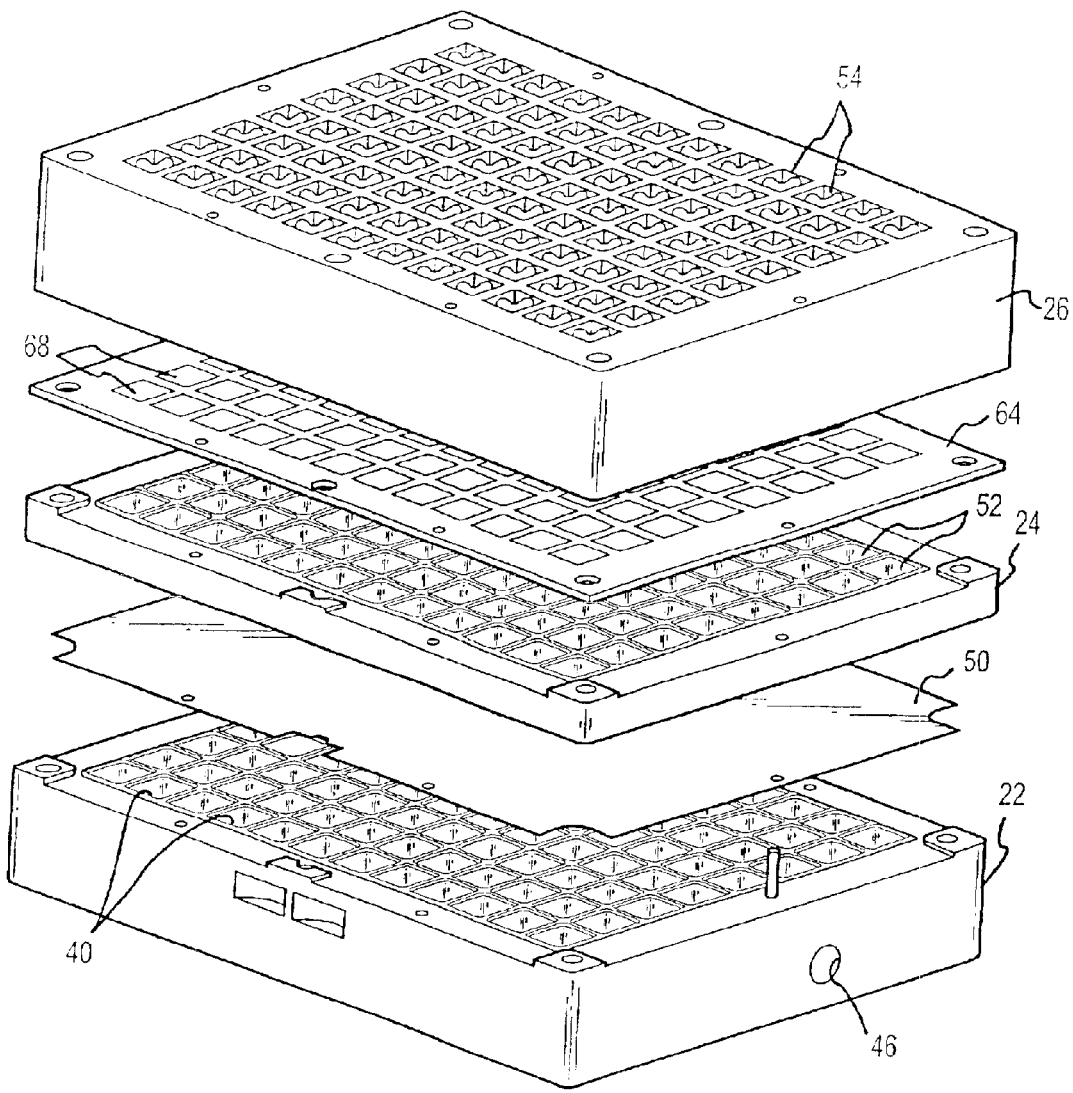
FIG. 1B is an exploded perspective of the apparatus of FIG. 1A with one porous sheet and a sealing sheet removed.
Figure 1C:
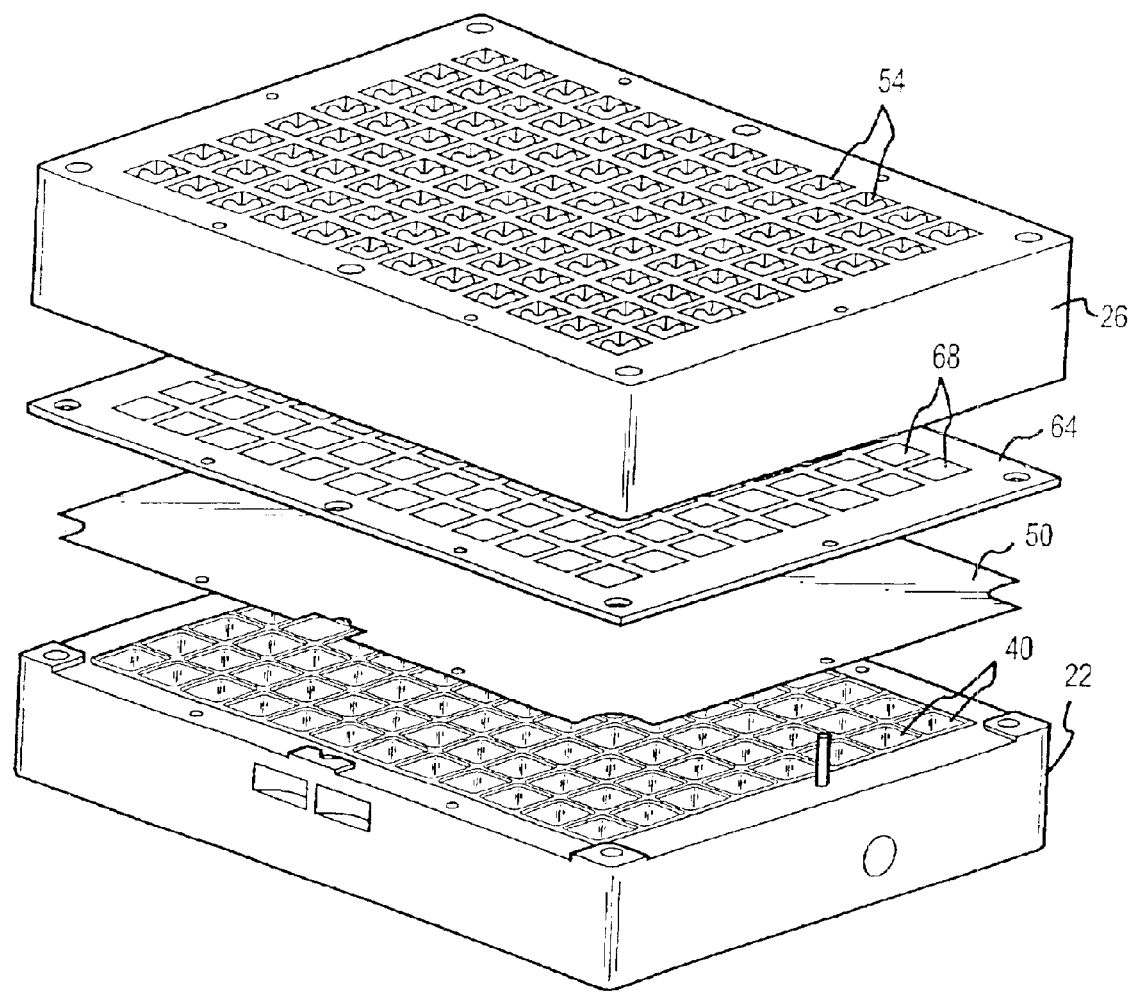
FIG. 1C is an exploded perspective of the apparatus of FIG. 1B with a central plate removed.

Referring now to the drawings, and first to FIGS. 1A, 1B, and 1C, an apparatus, generally indicated at 20, for use in testing a plurality of compositions in parallel is shown. The apparatus 20 may be used, for example, in testing fabric care chemicals such as anti-dye transfer polymers, dye absorbers, pretreatment agents, or stain guard agents. The fabric care chemicals may be used in laundry detergents or stain guard products used to pretreat clothing or other material such as upholstery. For example, the chemical composition may be optimized for use in cleaning dyed fabrics for removing soil and stains while retaining brightness and resisting dye loss from the fabric or dye transfer from one fabric to another. The compositions may be gas, liquid, or foam, or they may be solid or granular compounds designed to dissolve in water, for example. The compositions to be tested may also be located on the fabric with the same fluid used to test the various compositions. It is to be understood that the compositions and applications described herein are merely examples of uses for the apparatus and methods of the present invention, and that the invention may be used in other applications without departing from the scope of the invention. The apparatus and methods of the present invention may be used for applications in which it is desirable to create fluid movement through a porous medium or prevent fluid transfer between distinct regions of the porous medium.

As shown in FIG. 1A, the apparatus 20 includes a lower plate 22, central plate 24, upper plate 26, and cover plate 28, each having an array of openings. The plates 22, 24, 26, 28 are stacked with the openings in axial alignment with one another. The plates 22, 24, 26, 28 preferably include ninety-six openings (or multiples of ninety-six) arranged to correspond to a standard microtiter plate format. The number of test regions is preferably at least 4, 8, 15, 24, 40, 60, 90, 100, 200, 400, 500, 1000, 2000, 4,000, 10,000 or more. In preferred embodiments, the number of test regions=96*N, where N is an integer ranging from 1 to 100, preferably 1–10, and more preferably 1–5. Openings 30 extend through the corners of plates 22, 24, 26, 28 for receiving a screw, bolt, or other suitable attachment means 34 to hold the assembly together. The bolt 34 is preferably recessed within the lower plate 22 and cover plate 28 to prevent anything from protruding from the plates so that the apparatus can be used with equipment designed for devices having a conventional microplate format. The lower, central, and upper plates 22, 24, 26 also include alignment holes 60 for receiving an alignment pin 62 used to align components of the apparatus 20. The plates 22, 24, 26, 28 may have a thickness of between 0.063 and 6.0 inches and be formed from aluminum, titanium, steel, TEFLON, or nylon, for example. The plates (or block) 22, 24, 26, 28 may be formed as a solid piece or from a laminate construction. For example, openings may be formed in only a portion of the laminate layers so that the openings extend only partially through the plate. An upper surface of lower plate 22 may have a thin honeycomb structure which opens up to one large cavity 29 within a lower portion of the plate (FIG. 2D). The openings in the plates 22, 24, 26, 28 may be lined with an inert liner to prevent reactions between chemicals and the plate material. It is to be understood that the arrangement or number of openings and the material of the plates 22, 24, 26, 28 may be different than shown and described herein without departing from the scope of the invention. For example, the plates may have fewer than ninety-six reaction wells. Also, the position of the upper and lower plates 22, 26 may be switched (i.e., the apparatus may be used in an inverted position as compared to that shown in FIG. 1A).

Figure 2A:
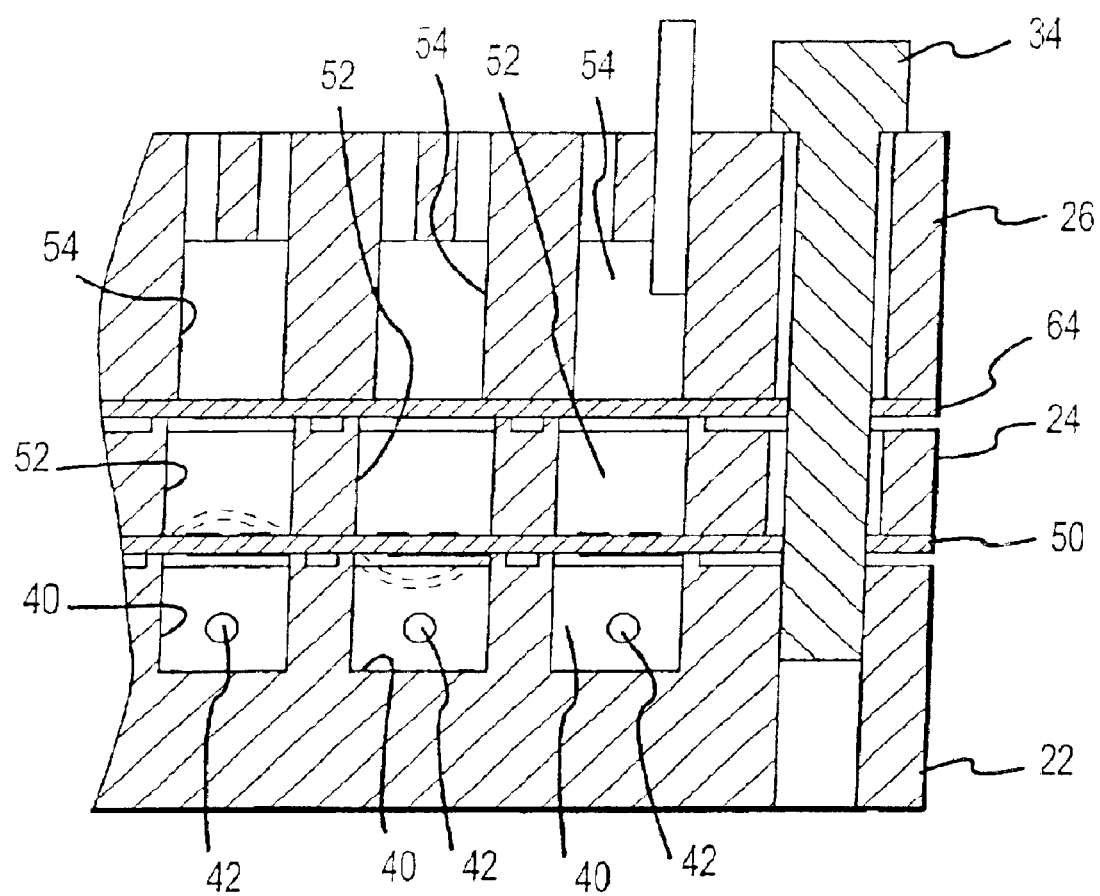
FIG. 2A is a partial cross-sectional view of the apparatus of FIG. 1B.

The openings in the lower plate 22 extend only partially through the plate to form cavities 40 which are interconnected with one another through passages 42 within the plate (FIGS. 1A and 2A). The passages 42 are connected to an inlet 46 for applying pressure or vacuum to the cavities 40 and a flexible membrane 50 interposed between the lower and central plates 22, 24, as further described below. The cavities 40 within the lower plate 22 are aligned with central fluid chambers 52 formed by the openings extending through the central plate 24. The openings extending through the upper plate 26 form upper fluid chambers 54 which are in alignment with both the central fluid chambers 52 and the cavities 40. The cover plate 28 includes a plurality of cylindrical openings 56 sized for receiving a pipette or similar tool for inserting fluid into the upper fluid chambers 54. The fluid chambers 52, 54 may each have a fluid volume of between 0.1 milliliters and 5 milliliters, for example.

The apparatus 20 further includes a sheet 64 interposed between the central plate 24 and the upper plate 26. The sheet 64 includes a plurality of test regions 68. The test regions 68 may all have the same composition for testing different compositions of the fluid or each of the fluid chambers 54 may contain the same fluid with the test regions each having different compositions contained thereon. As shown in FIG. 1A, the apparatus may include two sheets 64. One sheet may have white test regions and the other sheet may have dyed test regions, for example. The apparatus may also be configured to test the interaction between only a single sheet 64 and fluid within the fluid chambers 52, 54 as shown in FIG. 1B. The sheet 64 is preferably porous to allow fluid within the fluid chambers 52, 54 to pass therethrough. The sheet 64 may also be formed from a nonporous material in which case the fluid will not flow through the sheet, but will be agitated by pressurization of the fluid within the fluid chambers 52, as described below.

Figure 3:
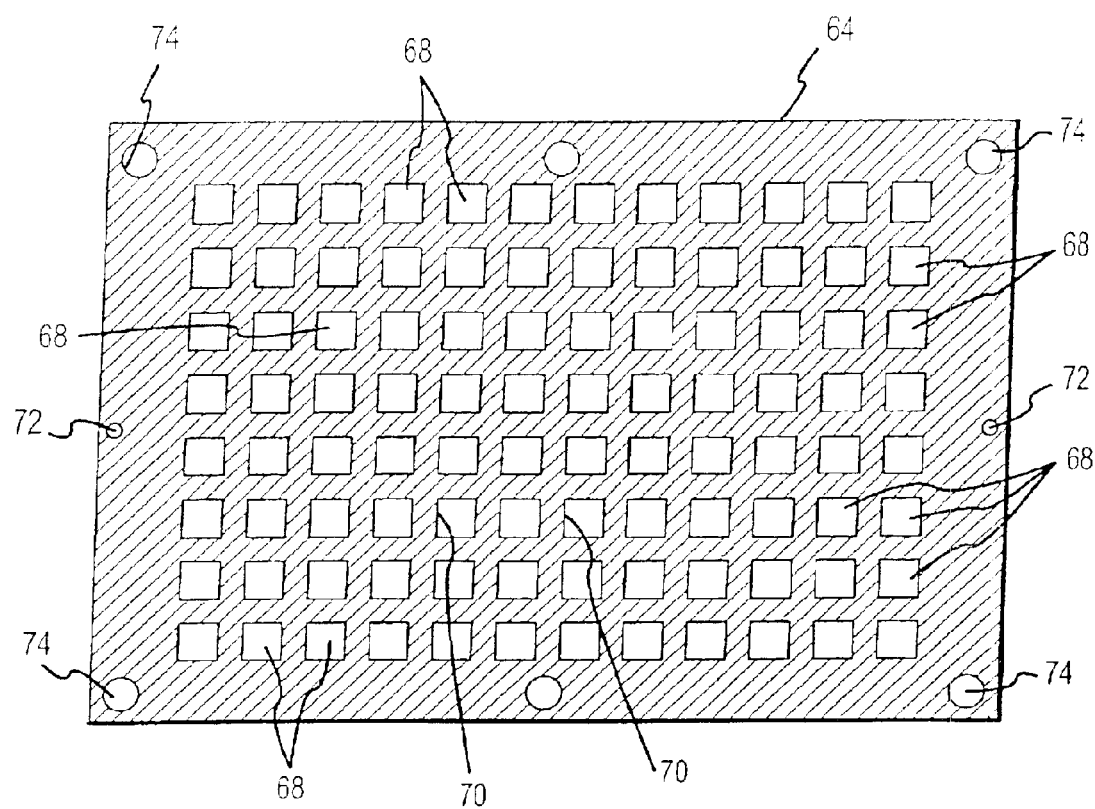
FIG. 3 is a plan view of a test fabric having seal material imprinted thereon for use with the apparatus of FIG. 1.

The porous sheet 64 may be formed at least partially from a fabric (e.g., cotton, polyester, rayon) silica, alumina, filter media (e.g., cellulose, quartz matte) ceramic, sintered metals, plastics or any other porous material or combination of materials. The porous material maybe woven fabric (e.g., 30–350 threads per inch), for example. The sheet 64 may be flexible or rigid. The sheet may also include non-porous regions having a porous material (e.g., fabric, catalyst, etc.) at or on the test regions. The sheet 64 includes alignment openings 72 for receiving the alignment pins 62 so that the test regions 68 in the sheet 64 can be properly aligned with the fluid chambers 52, 54 in the central and upper plates 24, 26, respectively (FIGS. 1 and 3). The sheet 64 also includes openings 74 for receiving screws 34.

As shown in FIG. 3, the porous sheet 64 includes a seal 70 which is integral with the porous material and separates the test regions 68. The seal 70 is applied to the fabric in a pattern to form test regions 68 corresponding generally in size and shape to the central and upper fluid chambers 52, 54, as viewed in transverse cross-section. The seal 70 defines the individual test regions 68 and prevents transfer of fluid between the test regions and cross talk of fluid between adjacent fluid chambers. When the test apparatus 20 is assembled, the periphery edges of the fluid chambers 52, 54 contact the seal 70 of the porous sheet 64 to prevent fluid from transferring between adjacent chambers either by seeping between the seal and chamber edges or bleeding through the fabric. Thus, continuous sheet 64 can be placed in contact with different solutions without cross contamination between the solutions and test regions 68 of the fabric. It is to be understood that the test regions may have shapes or sizes different than shown herein without departing from the scope of the invention. For example, the test regions, cavities, and fluid chambers may be circular, rectangular, oblong, triangular, or any other shape.

The seal 70 is formed from a material that penetrates the fabric to substantially fill the pores and can be physically or chemically solidified (e.g., cross-linked by some means such as curing to render it insoluble). The seal material is preferably selected so that it does not react with the test fluid and remains adhered to the porous material during testing and subsequent analysis. The seal 70 may be formed from a thermoplastic material that can be melted and flowed into fibers of the fabric to bond the sealing material to the fabric. Silk screening may also be used to bond the sealing material to the fabric. For example, the seal 70 may be formed from a plastisol ink available from Union ink of Ridgefield, N.J., under the trade name Ultrasoft. Plastisol ink is comprised primarily of PVC resin and a plasticizer. The ink wraps around the fibers and makes a mechanical bond with the fabric. If nylon material is used as the porous material, a bonding agent may need to be added to the seal material. When the plastisol is heated (e.g., 138–160° C.), the resin particles absorb the surrounding liquid (plasticizer) and swell to merge with one another to form a tough, elastic film. The ink may be applied by standard screen screening techniques, heat transfer printing, or molding, for example. The ink may also be cured by ultraviolet light or air dried instead of high temperature curing which may impact fabric strength or other fabric properties. It is to be understood that seal materials and methods for applying the seal 70 different than those described herein may be used without departing from the scope of the invention.

As shown in FIG. 1A, two porous sheets 64 may be placed at one time in the test apparatus 20 with an optional sealing sheet 76 placed in between the two porous sheets. The test regions 68 of one of the porous sheets 64 may optionally contain a dye (e.g., red colored dye) while the test regions of the other porous sheet are white. This allows the dye transfer between two fabrics to be analyzed. In applications such as pretreating test regions 68 or testing the cleaning ability of a detergent, only one porous sheet 64 is required (FIG. 1B). In some applications more than two porous sheets 64 (e.g., six sheets, greater than ten sheets) may be utilized with or without sealing sheets 76 interposed therebetween. The porous sheet 64 may be stained with oil or makeup, for example, to test the effectiveness of laundry detergent compositions. Other applications are described below. The sealing sheet 76 may also be placed between the porous sheets 64 and the central or upper plates 24, 26 (FIG. 1A). The sealing sheet 76 may be formed from a rubber material that is substantially nonporous and chemically inert to the compositions being tested. Openings 78 corresponding to the test regions 68 of the porous sheet 64 are punched or cut into the sealing sheet 76 to allow fluid flow therethrough. The sealing sheet 76 provides additional sealing between periphery edges of the fluid chambers 52, 54 and the porous sheet 64 or between two adjacent porous sheets. Alignment holes 80 are formed in the sealing sheet 76 to allow for proper alignment of the sealing sheet 76 with the porous sheets 64 and fluid chambers 52, 54.

Figure 4:
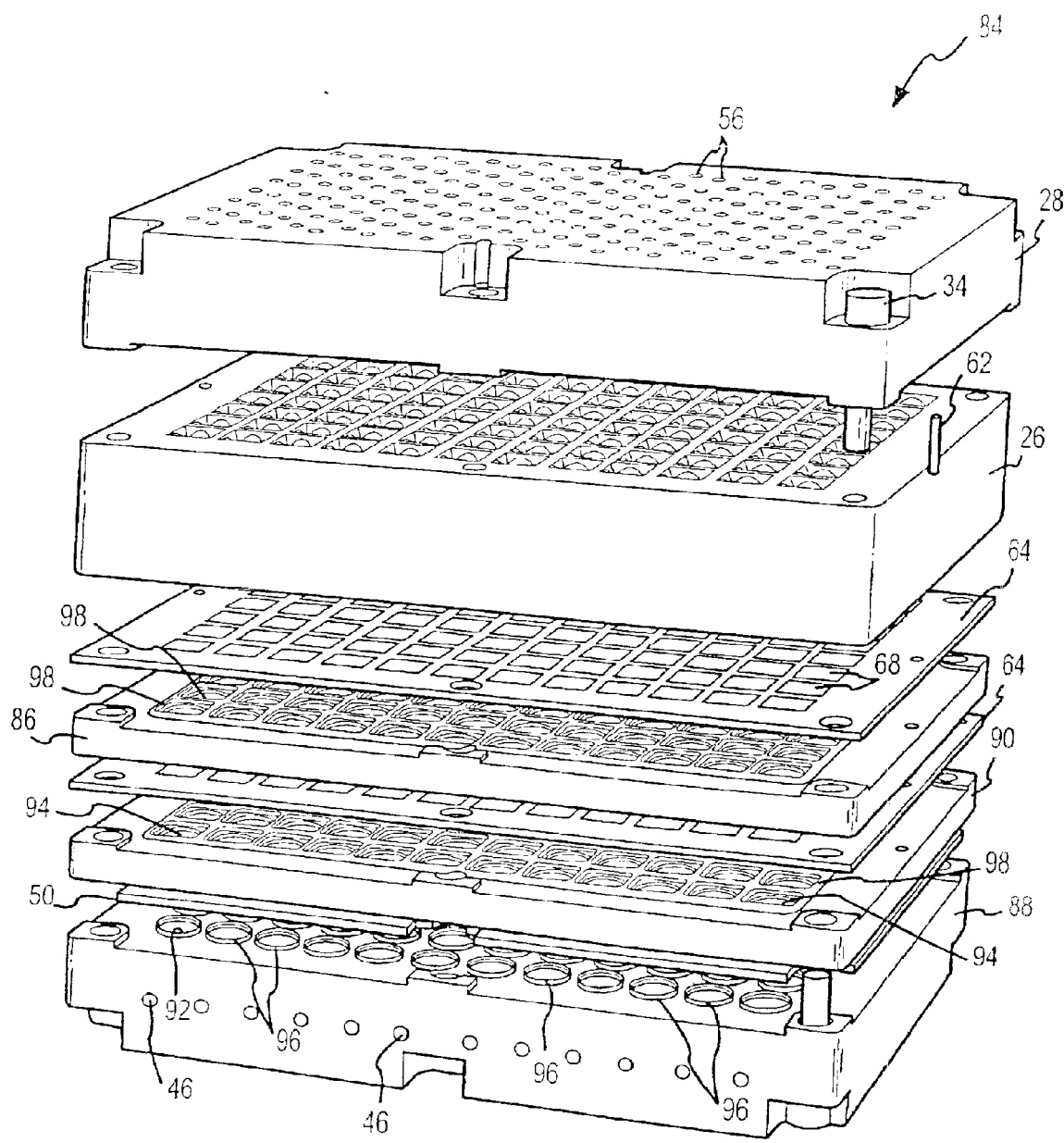
FIG. 4 is an exploded perspective of a second embodiment of the apparatus of the present invention.

FIG. 4 shows a second embodiment, generally indicated at 84, which is similar to the first embodiment 20 shown in FIG. 1A, except that a spacer block 86 is interposed between the two porous sheets 64. Also, lower plate 88 and central plate 90 include circular openings 92, 94 rather than the rectangular openings of the first embodiment 20. An upper surface of the lower plate 88 is machined with grooves extending around the periphery of openings 92 for receiving O-rings 96. The spacer block 86 and central plate 90 include raised edges (or O-rings) 98 extending around the openings 93, 94. The distance between the raised edges 98 is preferably the same as or larger than the width of the test regions 68 of the porous sheets 64 so that when the sheet is placed on top of the raised edges, the raised edges make contact with the seal 70 of the sheet. The spacer block 86 may also be used with the test apparatus 20 shown in FIG. 1A. Also, the circular openings may be used on only one of the plates 88, 90 or spacer block 86, or any combination thereof.

As previously described, the test regions 68 of the sheet 64 are preferably permeable to allow fluid to pass therethrough. In order to create fluid agitation, the fluid within chambers 52, 54 may be forced through the test regions 68 by applying a vacuum or pressure (or both) to the cavities 40 below the flexible membrane 50 (FIGS. 1A and 2A). A supply line providing pressure, vacuum, or both pressure and vacuum, is attached to the inlet 46 in the lower plate 22. The inlet 46 is in communication with the cavities 40 through the passages 42 formed in the lower plate 22. Fluid movement through the test regions 68 of the porous sheet 64 is caused by pressure or vacuum flexing the flexible membrane 50. When pressure is applied to the cavities 40, the flexible membrane flexes upwardly towards the porous sheet 64, thus increasing pressure in the central chambers 52 and forcing fluid from the central chambers into the upper chambers 54. When a vacuum is applied to cavities 40, the flexible membrane 50 is pulled downwardly into the cavities, thus decreasing pressure in the central chambers 52 and drawing fluid into the central chambers from the upper chambers 54. It is to be understood that rather than cycling between pressure and vacuum, only one of the pressure and vacuum may be cycled on and off. A second flexible membrane (not shown) may also be placed at the open end of the upper fluid chambers 54 and cycled with pressure and vacuum in conjunction with the application of pressure and vacuum to the lower cavities 40 to force the fluid through the test regions 68.

Figure 2B:
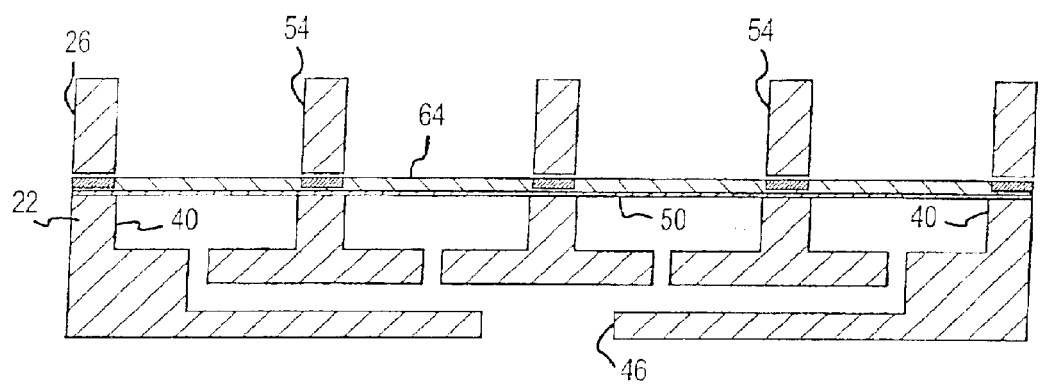
FIG. 2B is a cross-sectional view of the apparatus of FIG. 1C.
Figure 2C:
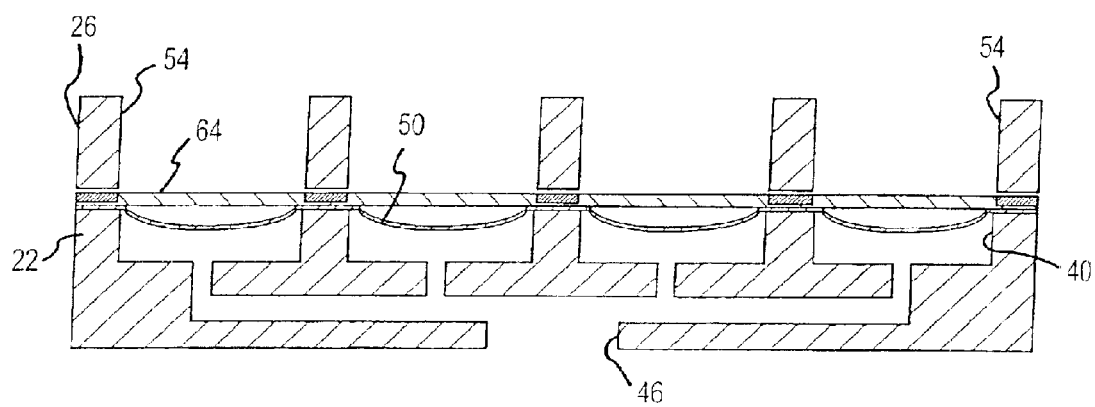
FIG. 2C is a cross-sectional view of the apparatus of FIG. 1C with a vacuum applied to cavities within the apparatus.
Figure 2D:
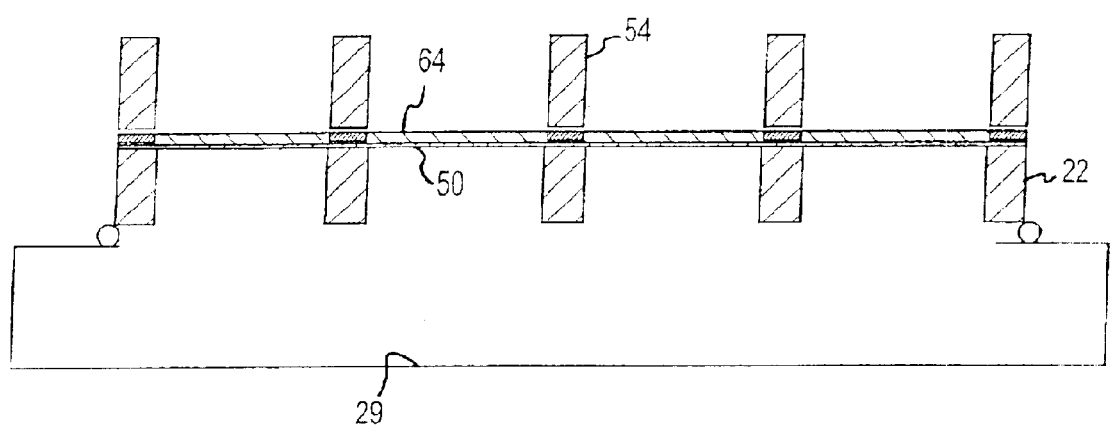
FIG. 2D is a cross-sectional view of the apparatus of FIG. 2B with fluid passages replaced with a common chamber.

As shown in FIGS. 1C and 2B, the central plate 24 may be removed and the porous sheet 64 positioned adjacent to the flexible membrane 50. The flexible membrane 50 is drawn away from the porous sheet 64 by the application of a vacuum to cavities 40 (FIG. 2C). A fluid volume is thus defined by the flexible membrane 50 and porous sheet 64 and the fluid is drawn through the porous sheet from the upper fluid chambers 54 into the lower fluid chambers 40 when a vacuum is created in the cavities. Fluid agitation is created by cycling the vacuum (and pressure) on and off to force the fluid back and forth through the porous sheet 64.

Pressure may also be applied to the upper chambers 54 to force the fluid through the porous sheet and cause the flexible membrane 50 to flex and provide a space for the fluid. The pressure applied to the upper chambers may also be cycled on and off to force the fluid back and forth through the porous sheet 64.

Figure 2E:
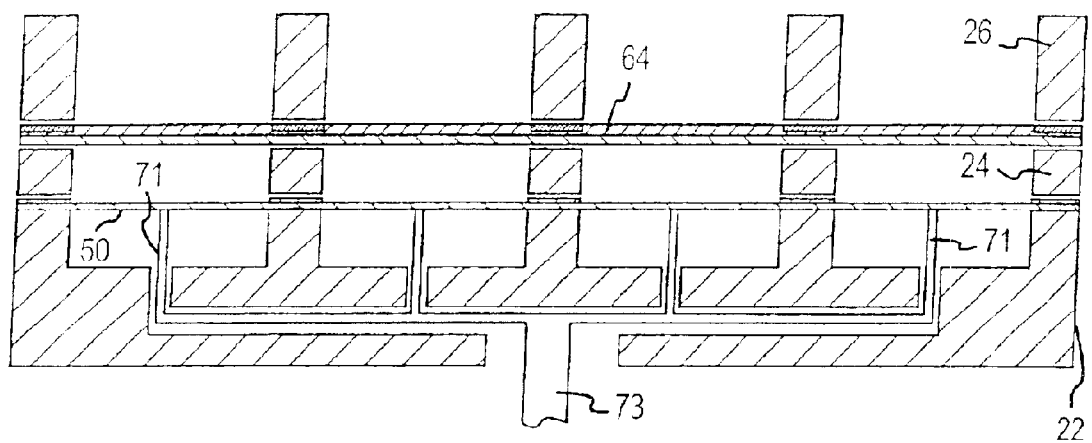
FIG. 2E is a cross-sectional view of the apparatus of FIG. 2A with movable rods attached to a flexible membrane to flex the membrane.

The membrane 50 may also be flexed by mechanical means rather than by applying a pressure or vacuum. For example, push-pull rods 71 may be attached to the membrane 50 at a location within each of the cavities 40 of the lower plate, as shown in FIG. 2E. The rods are fixedly attached to a central actuator 73 which operates to move each of the rods axially to flex the membrane 50 towards and away from the porous sheet 64. The actuator may be a linear or rotary actuator and powered by pneumatic, hydraulic, or electrical means, for example. The rods 71 may each have a piston at an upper end thereof to contact a larger surface area of the membrane 50, for example. The rods 71 may be coupled to the membrane 50 by adhesive or other attachment means so that the rods can move the membrane in opposite directions, or the rods may be separate from the membrane and used only to flex the membrane in a direction towards the porous sheet 64.

The flexible membrane 50 is preferably formed from an elastic material that is nonporous and chemically inert to the compositions being tested. For example, the membrane 50 may be formed from silicone, latex, or nitrite and have a thickness of 0.004–0.010 inches. The membrane 50 is preferably sufficiently flexible (e.g., capable of stretching at least 400% of its resting state length) so that it can extend at least partially into the central fluid chamber 52 (as shown in phantom in the left chamber in FIG. 2A) and into the cavity 40 (as shown in phantom in the center cavity in FIG. 2A). The membrane may also be preformed so that the membrane can flex without requiring significant stretching of the material. The membrane 50 may deflect longitudinally approximately 1 mm to 10 mm into chamber 52 or cavity 40 to displace approximately 0.01 ml to 1 ml of fluid.

Figure 5:
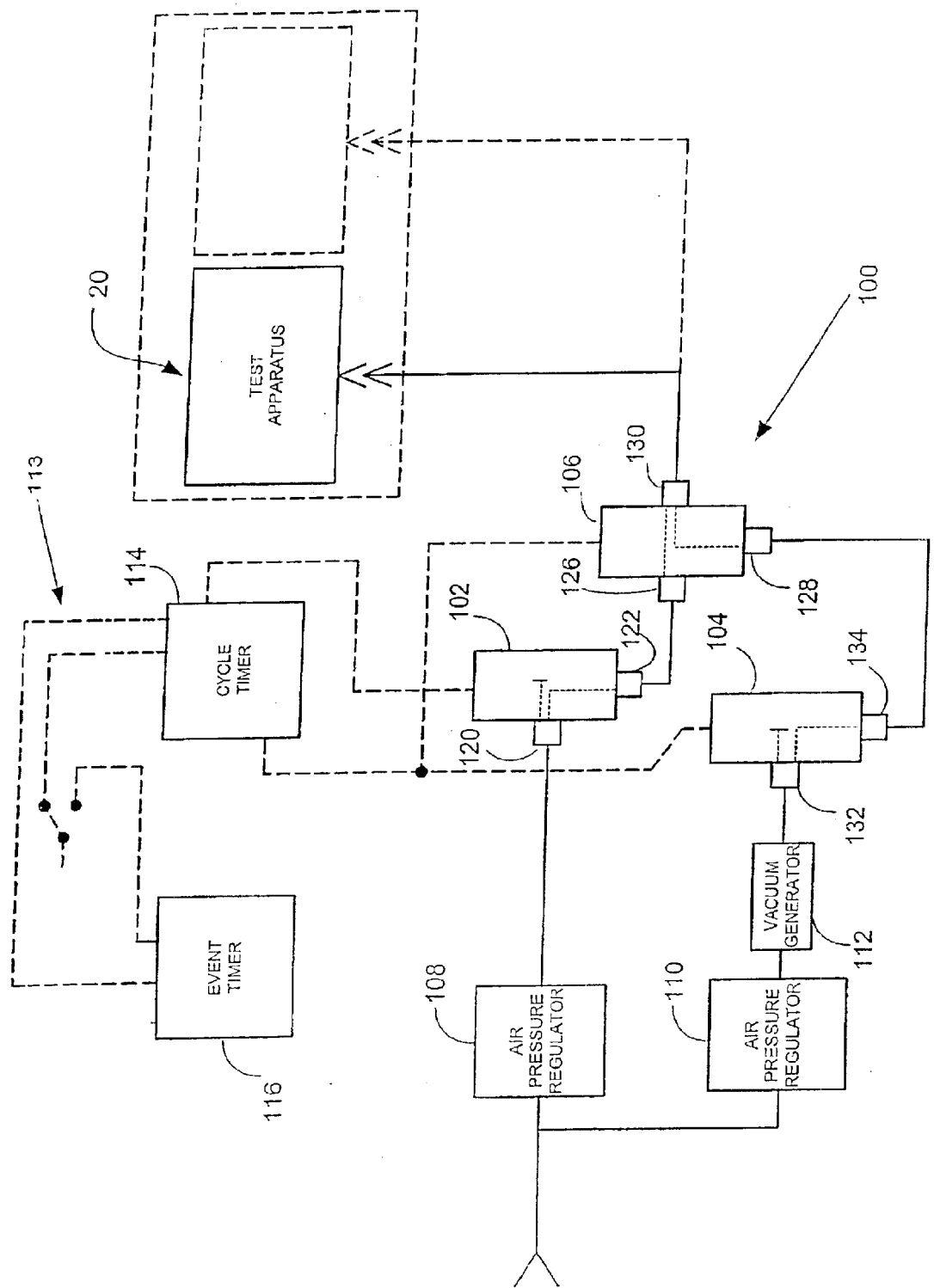
FIG. 5 is a schematic of a pneumatic circuit used to apply pressure to the apparatus of FIGS. 1 and 4.

FIG. 5 illustrates an example of a pneumatic circuit 100 that may be used to apply pressure and vacuum to the apparatus 20, 84. The circuit includes three solenoid valves 102, 104, 106, air pressure regulators 108, 110, a vacuum generator 112, and an electronic controller, generally indicated at 113. The electronic controller 113 includes a cycle timer 114, which controls the solenoid valves 102, 104, 106 and an event timer 116. The event timer 116 starts the cycle timer 114 at the beginning of the test and stops the cycle timer at the end of the test. The cycle timer 114 sequentially opens and closes the pressure and vacuum solenoid valves 102, 104 and changes position of the control solenoid valve 106 to provide pressure and vacuum to the test apparatus 20. Pressurized air (e.g., 80–100 psig.) is provided to the circuit 100 from an external source (not shown). Pressure regulator 108 is positioned upstream of pressure solenoid valve 102, which includes an inlet port 120 and an outlet port 122. When the pressure solenoid valve 102 is energized it connects ports 120 and 122 to provide flow to control solenoid valve 106, which ports pressure from inlet port 126 to outlet port 130 in its pressure position. Pressure regulator 110 is positioned upstream of vacuum solenoid valve 104 which includes inlet port 132 and outlet port 134. The vacuum generator 112 is positioned between the pressure regulator 110 and the vacuum solenoid valve 104 to create approximately 25 inch Hg of vacuum. The vacuum solenoid valve 104 supplies a vacuum at port 134, which is connected to the control solenoid valve 106, when the vacuum solenoid is in its energized position. The control solenoid valve 106 connects ports 128 and 130 when in its vacuum position to provide a vacuum to the test apparatus 20.

The cycle timer 114 is preferably programmed to first energize the vacuum solenoid valve 104 and place the control solenoid valve 106 in its vacuum position (connecting ports 128 and 130) while deenergizing the pressure solenoid valve 102. The cycle timer 114 next energizes the pressure solenoid valve 102 and places the control solenoid valve 106 in its pressure position (connecting ports 126 and 130), while deenergizing the vacuum solenoid valve 104. The event timer 116 may run the cycle timer 114 through 1800 to 3600 pressure and vacuum cycles, with each cycle lasting approximately ½ second, for example. It is to be understood that the circuit 100 shown in FIG. 5 and the operation described herein are provided for purposes of illustration only. One of ordinary skill in the art will readily appreciate that other systems may be used to supply pressure and vacuum to the test apparatus 20. For example, liquid may be used to pressurize the cavities 40 instead of gas.

Figure 6:
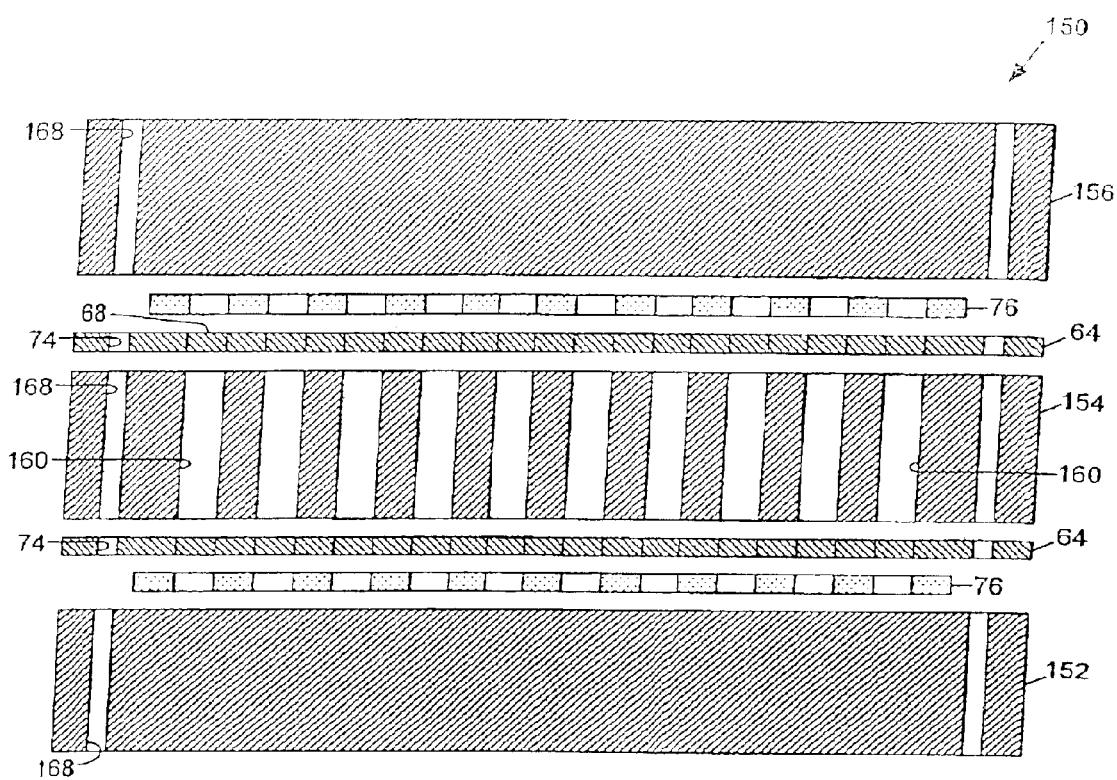
FIG. 6 is a cross-sectional view of a third embodiment of the apparatus of the present invention.

A third embodiment of the test apparatus is shown in FIG. 6 and generally indicated at 150. The apparatus includes a lower plate 152, a central plate 154, and an upper plate 156. Central plate 154 includes an array of openings extending therethrough to form fluid chambers 160. In one embodiment, a first porous sheet 64 is placed between the lower plate 152 and central plate 154, and an optional second porous sheet is placed between the central plate 154 and upper plate 156. Optional sealing sheets 76 are placed between the lower plate 152 and the first porous sheet 64, and upper plate 156 and the second porous sheet. Each plate 152, 154, 156 includes openings 168 for receiving screws or other suitable attachment means. In order to assemble apparatus 150, the optional sealing sheet 76 and first porous sheet 64 are placed on top of the lower plate 152. The central plate 154 is then positioned over the first porous sheet 64. The test fluids are placed into their respective fluid chambers 160 and the second porous sheet 64 and sealing sheet 76 are placed over the central plate 154. The upper plate 156 is positioned over the sealing sheet 76 and screws (not shown) are inserted into the aligned holes 74, 168 in each of the porous sheets 64 and plates 152, 154, 156 to force each component into contact with its adjacent component. The assembly 150 may be placed on a shaker or rocker to agitate the fluid and increase contact between the fluid particles and the test regions 68. Mixing balls may also be inserted into each fluid chamber 160 to agitate the fluid. An array of parallel plungers (e.g., syringes) (not shown) may be used to agitate the fluid. The syringes may be used to pressurize fluid similar to the flexible membrane of the previous embodiments.

The apparatus may be inserted into a test station which includes connections for pneumatic supply lines and temperature control. For example, a test station may comprise a base sized for receiving a plurality of test blocks (e.g., four test apparatuses). The pressure/vacuum inlet may be located on a bottom surface of the lower plate 22 and aligned with a pressure/vacuum coupling on a bottom of the base. The pressure/vacuum coupling is in fluid communication with a supply line connected to the base. The base may also be configured for heating the test blocks. The test station may also include a cover (e.g., a clear plastic plate) that is placed over the test blocks and attached to the base of the test station. The cover may include an opening for receiving pressure for pressurizing fluid within the fluid chambers 54 to force the fluid through the porous sheet 64. The test stations facilitate quick connection and removal of the test blocks from the pneumatic supply and allow for testing of multiple test blocks at one time.

Figure 7A:
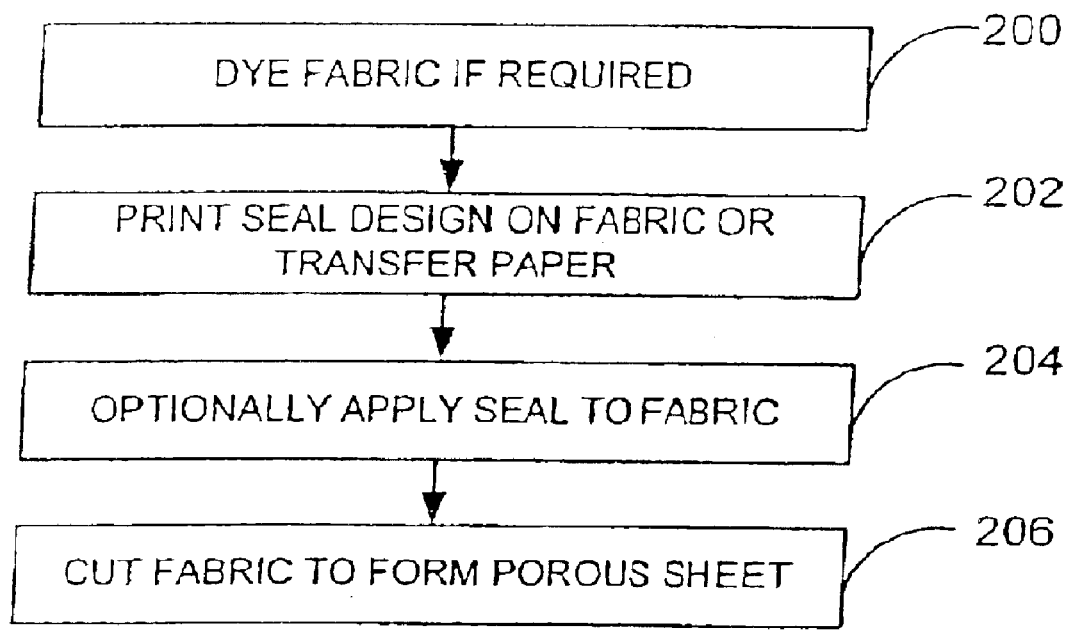
FIG. 7A is a flowchart illustrating a process for preparing a test sheet.
Figure 7B:
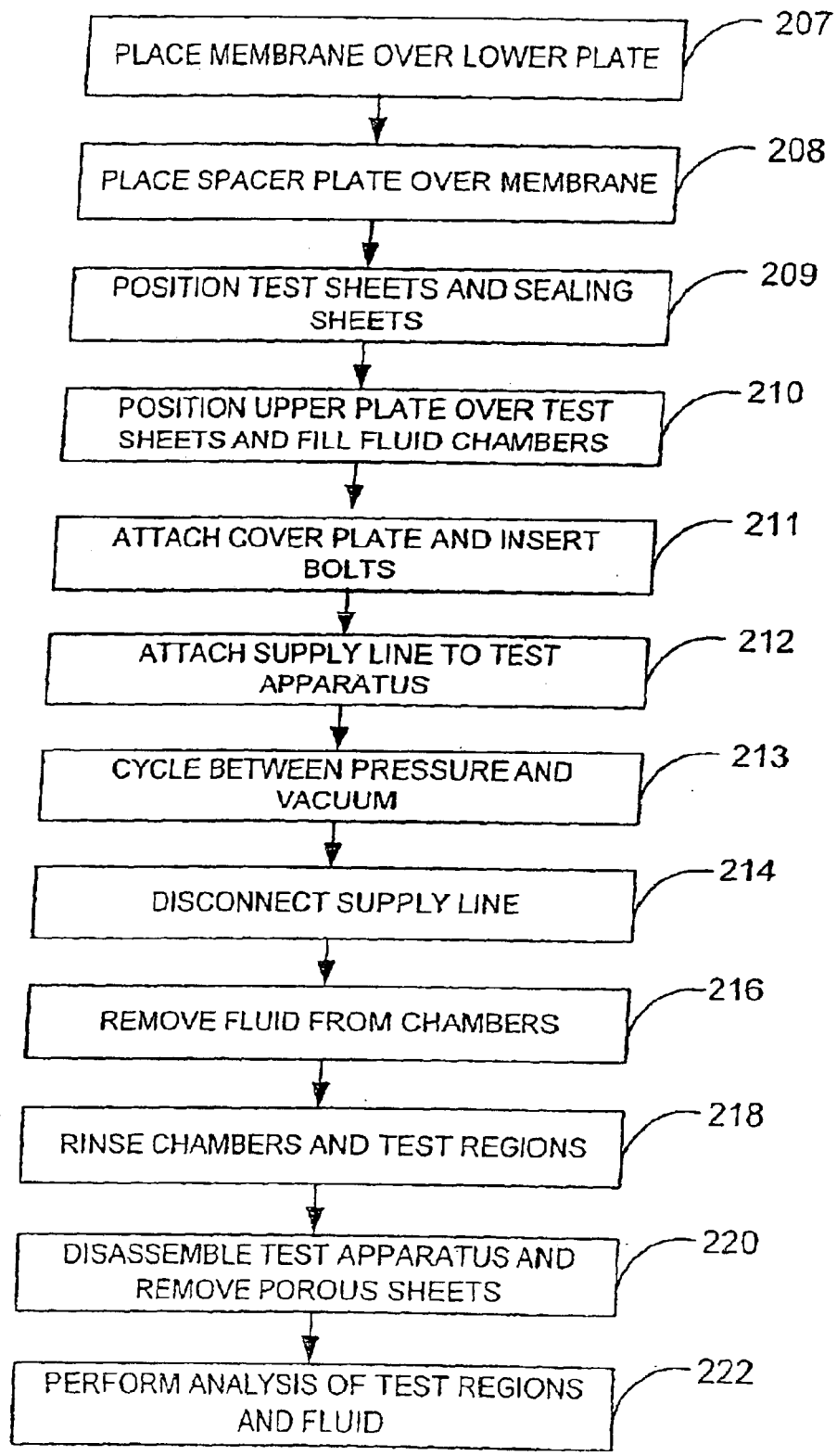
FIG. 7B is a flowchart illustrating a process for testing compositions with the apparatus of FIGS. 1 and 4.
Figure 8:
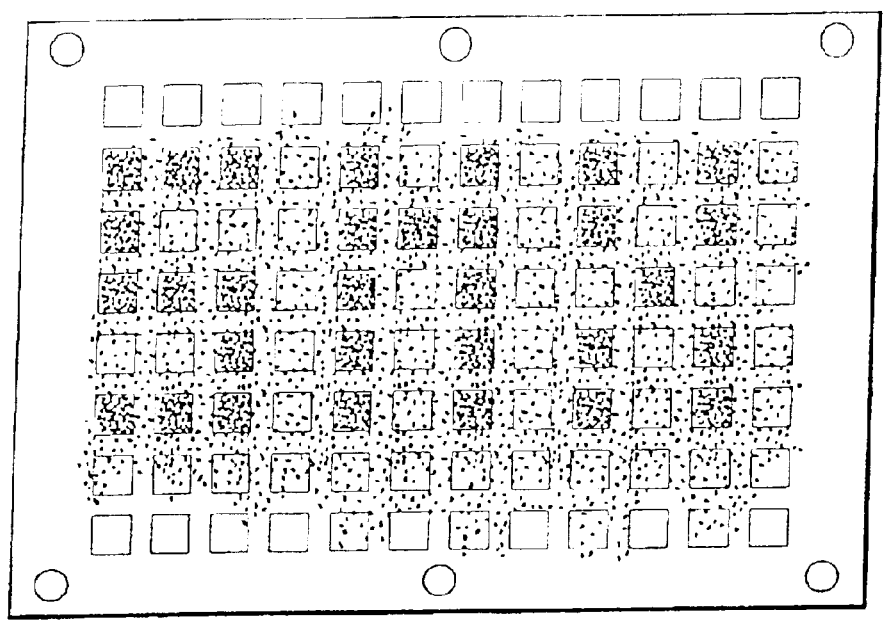
FIG. 8 is a plan view of a test sheet without an integral seal used in a first experiment (IA).
Figure 9:
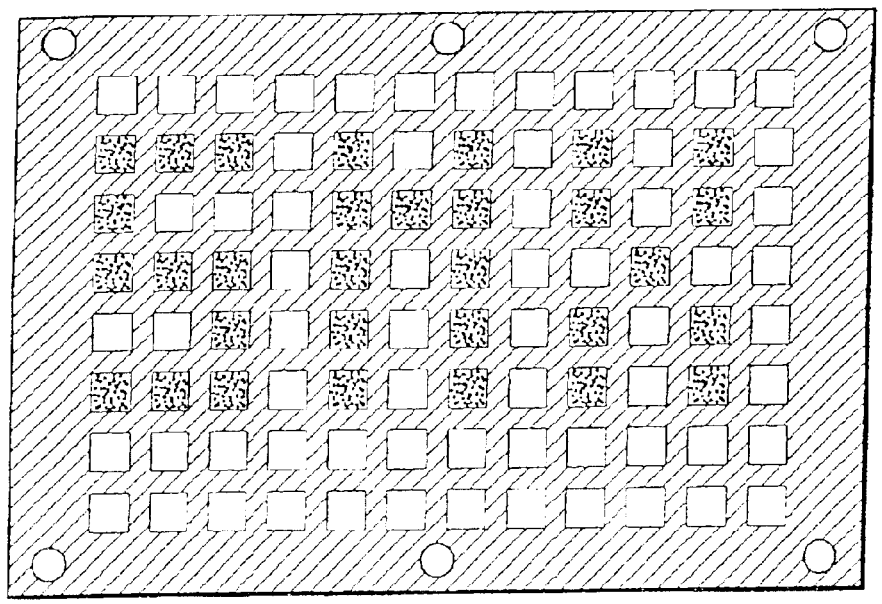
FIG. 9 is a plan view of a test sheet with an integral seal used in a second experiment (IB).
Figure 10:
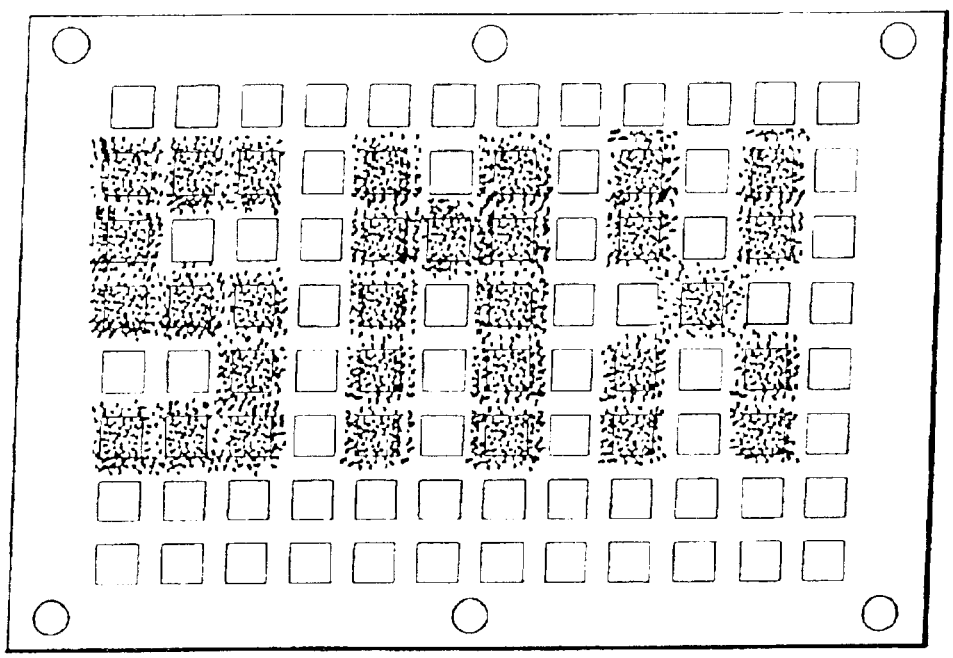
FIG. 10 is a plan view of a test sheet without an integral seal used in a third experiment (IIA).
Figure 11:
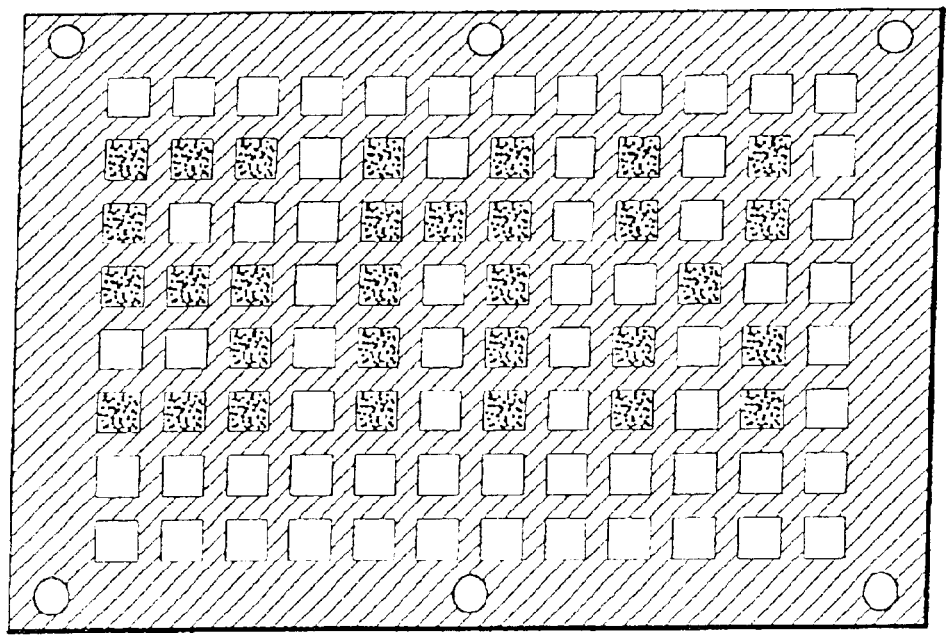
FIG. 11 is a plan view of a test sheet with an integral seal used in a fourth experiment (IIB).

FIG. 7A is a flowchart illustrating a process for preparing a test sheet and FIG. 7B is a flowchart illustrating a process for testing a plurality of compositions in parallel using the apparatus shown in FIGS. 1A, 1B, 1C, or 4. The fabric is first dyed if the test regions 68 of the porous sheet 64 are to be colored (step 200). The design shown in FIG. 3 is printed with the seal material on transfer paper (step 202). The transfer paper is passed through a conveyer dryer or other suitable curing equipment where the seal material is heated until it has gelled enough to be dry to the touch. The printed transfer paper is next placed in a press adjacent to the fabric. Heat and pressure is applied to the print and fabric to force the seal material into the fabric and complete the curing process (step 204). The press is then opened and the paper is peeled off of the fabric with the seal 70 remaining on the fabric. The fabric may then be cut to form individual porous sheets 64 (step 206). A template cutter may be used to punch alignment and screw holes 72, 74 into the porous sheets 64. It is to be understood that processes different than those described herein may be used to form the test sheet 64 without departing from the scope of the invention. For example, the seal may be applied directly to the fabric without the use of transfer paper and heat cured or dried by exposure to light or air. In particular, screen print methods may be used as described below in Example 1.

The apparatus 20 is then assembled as generally shown in FIGS. 1A, 1B, and 1C (depending on the embodiment). The flexible membrane 50 is first positioned over the lower plate 22 with the alignment pins 62 extending through the alignment holes in the membrane at step 207 (FIG. 7B). The central plate 24 is next placed (if used) over the flexible membrane 50 (step 208). One or more porous sheets 64 along with one or more optional sealing sheets 76 are placed over the central plate 24 using the alignment holes 72, 80 and pins 62 to align the sheets with the plate (step 209). The upper plate 26 is placed over the porous sheets 64 and test samples are placed within each of the upper fluid chambers 54 (step 210). The cover plate 28 is optionally placed on top of the upper plate and screws 34 are then inserted into the aligned openings 30, 74 and tightened to force the sheets 64 into sealing engagement with the adjacent plates 24, 26 (step 211). The apparatus may be optionally placed into an oven or heating block to preheat the fluid to approximately 40° C., for example.

The circuit 100 is connected to the inlet 46 of the apparatus at step 212 (FIGS. 1A, 5, and 7). The event timer 116 is started and the circuit 100 provides pressure and vacuum to the cavities 40 (step 213). After the cycles are completed, the circuit 100 is disconnected from the apparatus and the cover plate 28 (if in place) is removed (step 214). A sample of each test fluid is removed from the upper fluid chambers 54. The remaining fluid is then removed by turning the apparatus 20 upside down and allowing the fluid to drain from the upper fluid chambers 54 (step 216). The chambers 54 may also be rinsed to ensure that all the test fluid is removed (step 218). The apparatus 20 may then be left to sit assembled for a period of time to allow the test regions 68 to dry to prevent fluid from transferring between adjacent test regions when the apparatus is disassembled. After the porous sheet 64 has dried, the apparatus 20 is disassembled and the porous sheets removed (step 220).

The test regions 68 may be visually examined to provide qualitative results and scanned to obtain reflectance spectra data for quantitative analysis (step 222). The spectral reflectance may be used to derive color density values and colorimetric parameters, for example. The liquid removed from the individual wells may also be analyzed to determine the amount of dye that was removed from the fabric during the test.

The apparatus 20, 84, 150 may be used to test a plurality of agents having varying compositions so that the compositions can be quickly narrowed down to the most effective formulations. For example, the apparatus 20, 84, 150 may be used to select a particular polymer, determine the best concentration, and adjust a ratio of surfactants. The compositions exhibiting the most favorable results may then be put through additional testing, such as by placing a large piece of fabric in a container filled with the solution and shaking the container, or placing the fabric in a conventional washing machine.

In a preferred application, the aforedescribed apparatus may be used in a combinatorial, high-throughput research program directed to developing improved fabric-care compositions or components thereof, improved fabric treatments, improved fabric compositions, or directed to other research goals, such as fabric-care process characterization and/or optimization. Fabric-care compositions are compositions of matter comprising one or more components having or potentially having utility in connection with a fabric care application. Exemplary fabric-care compositions include compositions comprising various laundry aids such as detergents, soaps, bleaches and softeners, among others. Hence, fabric-care compositions (and likewise, the test fluids used in the research program) can include components that are elements, compounds or compositions, and can typically include, without limitation, polymers, surfactants, dyes, bleaches, perfumes, buffers, electrolytes, builders, sequestering agents, flame retardants, and/or enzymes alone or in various combinations and permutations. The fabric care compositions are preferably liquids (e.g., solutions, dispersions, or emulsions), but can also be solids or, in some applications, gases.

Combinatorial (i.e., high-throughput) approaches for screening a libraries of materials for applications as components of fabric-care compositions may include an initial, primary screening, in which various test fluids and/or fabrics are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics or properties of a known or standard fabric care compositions or of a known fabrics. Because local performance maxima may exist in compositional spaces between those evaluated in the primary screening of the first libraries or alternatively, in process-condition spaces different from those considered in the first screening, it may be advantageous to screen more focused candidate libraries (e.g., libraries focused on a smaller range of compositional gradients, or libraries comprising test fluids or fabrics having incrementally smaller compositional variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused candidate libraries can continue as long as the high-throughput primary screen can meaningfully distinguish between neighboring library compositions or compounds.

Once one or more hits have been satisfactorily identified based on the primary screening, fabric care composition libraries focused around the primary-screen hits can be evaluated with a secondary screen—a screen designed to provide (and typically verified, based on known materials, to provide) process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen.

Particular fabric care composition components (e.g., surfactants, polymers, etc. as more fully described below), fabrics, and/or processing conditions having characteristics that surpass the predetermined metrics for the secondary screen may then be considered to be "leads." If desired, additional candidate libraries focused about such lead materials can be screened with additional secondary screens or with tertiary screens. Identified leads (compositions or process conditions) may be subsequently developed for commercial applications through traditional bench-scale and/or pilot scale experiments.

While the concept of primary screens and secondary screens as outlined above provides a valuable combinatorial research model for investigating fabric care compositions, components thereof, fabric treatments, fabric compositions, fabric treatments and/or process conditions, a secondary screen may not be necessary for certain situations in which primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary or a secondary screen, depending on the specific research program and goals thereof.

In one generally preferred approach, a test sheet of fabric 64 comprising a plurality of test regions 68 is provided (FIG. 3). Each of the plurality of test regions 68 is simultaneously contacted with a different test fluid, and the plurality of test regions and/or the plurality of contacted test fluids are then screened, preferably simultaneously screened, for a property of interest with respect to fabric care (i.e., a fabric property of interest) to evaluate the relative efficacy of the different test fluids with respect to that property of interest. In this test-fluid varying embodiment, the plurality of test regions 68 preferably comprises the same, or substantially the same fabric composition, such that the differences in test fluid can be directly evaluated. The plurality of test regions 68 may alternatively comprise different fabric compositions, such that differences in test fluids and differences in fabric composition (e.g., fabric pretreatments) can be evaluated in a single experiment. The plurality of test regions 68 of the test sheet of fabric are preferably substantially isolated from each other.

A non-limiting example of this approach may include simultaneously contacting a plurality of test regions 68 of the same dyed test sheet of fabric with different dye-affecting agents—such as dye-fixing agents or anti-dye-transfer agents. Following such contact, the plurality of test regions 68 can be screened, for example, to determine the effectiveness of the dye-fixing agents. Additionally or alternatively, the differing contacted test fluids can be screened, for example, to determine the effectiveness of the anti-dye-transfer agents (e.g., by evaluating whether the anti-dye-transfer agents scavenged released dyes into solution). As explained below, other fabric care compositions and/or components or ingredients thereof can likewise be evaluated after such simultaneous contact with an appropriate screening methodology.

In another generally preferred approach, a test sheet of fabric 64 comprising a plurality of test regions 68 is provided, where each of the plurality of test regions comprises a different fabric composition (e.g., differently treated regions of fabric sheet). As discussed below, the differing fabric compositions at the plurality of test regions 68 are preferably prepared by simultaneously contacting each of test regions with different treatment fluids, and allowing the differing treatment fluids (or components thereof) to interact with (e.g., adsorb, covalently bond, hydrogen bond, or ionic bond to or with) the fabric at each of the plurality of test regions. Each of the plurality of test regions 68 (and hence, each of a plurality of different fabric compositions) is simultaneously contacted with a test fluid, and preferably with the same or substantially the same test fluid. The plurality of test regions 68 are then screened for a fabric property of interest to evaluate the relative efficacy of the different fabric compositions. This general approach can be referred to hereinafter as a fabric-composition varying embodiment.

A non-limiting example of this generally-preferred approach may include simultaneously treating a plurality of test regions 68 of a test sheet of fabric 64 with varying treatment agents (e.g., soil-inhibiting agents) to form a test sheet of fabric comprising different fabric compositions at different test regions. The plurality of varying fabric compositions can then each be screened for resistance to soiling by contacting, and preferably simultaneously contacting the plurality of fabric compositions with a soiling agent (preferably the same soiling agent), and then evaluating the effectiveness of the differing soil-inhibiting agents with respect to that soiling agent.

In especially preferred variations of the immediately aforementioned preferred approaches (i.e., the test-fluid varying embodiment and/or the fabric-composition varying embodiment), two or more test sheets of fabric 64 are provided, with each of the two or more test sheets of fabric comprising a plurality of test regions 68, and conversely, with each of the plurality of test regions comprising two or more test sheets of fabric. The two or more test sheets of fabric 64 can be the same or different from each other (i.e., can be the of the same or different types of fabric and/or fabric compositions). In some applications, the two or more test sheets of fabric are different from each other such that the potential for various interactions between the two or more test sheets of fabric can be evaluated at the corresponding test regions. As an exemplary, non-limiting application, a white test sheet of fabric and a colored test sheet of fabric can screened as described in the aforementioned preferred approaches, and the extent of dye transfer between the first white test sheet of fabric and the second colored test sheet of fabric can be determined for various test fluids and/or for various fabric compositions. The two or more test sheets of fabric can, in this embodiment, be three or more, four or more, five or more, six or more or seven or more test sheets of fabric 64. The number of test sheets of fabric employed in combination ranges from about 2 to about 20 or more, preferably from 2 to about 10 and most preferably from 2 to about 7. Regardless of the exact number of test sheets of fabric employed, the two or more (or 3 or more, etc.) test sheets of fabric 64 preferably each comprise an integral seal 70 that isolates the plurality of test regions 68 on each of the two or more (or 3 or more, etc.) test sheets of fabric.

The test sheet of fabric 64 can generally comprise any type of fabric, including both woven and non-woven fabrics, and/or natural and man-made fabrics. The test sheet of fabric 64 is preferably a fabric used for garments (e.g., clothing, coats, etc.), for linens (e.g., towels, bed sheets, etc.), for furniture, for draperies, and/or for other applications. Preferred fabric materials for the test sheet of fabric include fabrics comprising natural materials such as cotton, wool, leather or silk, among others, or man-made materials such as polyester, nylon, rayon, lycra or Gore-Tex™, among others.

The plurality of regions 68 of the test sheet of fabric 64 are preferably isolated, or at least substantially isolated, from each other while being contacted with the test fluid. As used herein, a plurality of adjacent test regions of a common test sheet of fabric are substantially isolated from each other if a test fluid contacted with a first test region does not substantially diffuse (e.g., bleed-through) to, or otherwise become exposed to, a second, adjacent, test region during the simultaneous contacting step. The extent of diffusion (e.g., bleed-through) of the test fluid(s) between adjacent test regions is preferably sufficiently small so as not to appreciably affect determination of the fabric property of interest for adjacent regions. In preferred embodiments, the plurality of adjacent test regions 68 are completely isolated from each other, such that a first test fluid sample can be contacted with a first test region and a second test fluid sample can be contacted with a second test region during the simultaneous contacting step without any detectable affect on the determination of the fabric property of interest for the adjacent regions.

In especially preferred embodiments, the plurality of regions 68 are isolated from each other using a seal, external to the test sheet of fabric or integral therewith, together with the apparatus described above or other suitable device. The integral seal as disclosed herein can provide substantially complete isolation between the wells, and therefore, between adjacent regions of the test sheets of fabric—even where the regions of the test sheet of fabric are exposed to the test fluids over long periods of time (e.g., even over an hour or more). Moreover, the integral seal is substantially robust with respect to application—in that it can provide substantial isolation of test regions of the test sheet of fabric without being particularly sensitive to variations in fabric types or properties, variations in test fluid compositions or properties, device configuration and/or variations in well-filling protocols (e.g., simultaneous, rapid serial, and/or slow-serial (e.g. in which adjacent wells are empty/filled and capillary forces (e.g. wicking) can be relatively strong)). The integral seal is advantageous, in particular, in applications where test sheets of fabric lacking an integral seal and/or lacking an external seal may otherwise demonstrate cross-talk between adjacent regions under the conditions and filling protocols of the experiment.

The plurality of regions can, however, in some embodiments and applications, be isolated from each other without using an integral seal and/or without using any seal. In a preferred embodiment, one or more test sheets of fabric lacking an integral seal, can be used in an apparatus of the present invention providing enhanced compression between adjacent wells (e.g., having raised ridges 96 between each of the wells on one or both of the plates adjacent the one or more test sheets of fabric, as described above and shown in FIG. 4). Without being bound by theory not specifically recited in the claims, the compression-enhancing features (e.g., raised ridges) focus the pressure applied by the screws onto very narrow inter-well regions, such that the fabric in these inter-well regions is strongly compressed between each of the adjacent test regions of the test sheet. The inter-well compression of the test sheets of fabric greatly reduces the pore space available and thus serves to greatly slow down the diffusion of liquid from one cell to the next by reducing the effective cross section of the pores available for diffusion. In a preferred filling protocol, fairly good isolation between test regions of the test sheet can be achieved in a configuration comprising one or more test sheets of fabric, even where such test sheets lack integral seals, where the wells are filled substantially simultaneously or in rapid serial fashion, such that a filled well is not adjacent to an empty well for a period of time sufficient to cause undesired wicking and associated cross-talk between adjacent regions of the test sheet of fabric. The actual time that adjacent empty and filled wells can coexist will vary depending on several factors, including fabric properties, test fluid properties, and the particular apparatus employed in the screening, as discussed below. In a particularly preferred approach, inter-well compression can be combined with the substantially simultaneous or rapid serial filling of adjacent wells—thereby minimizing and preferably substantially avoiding cross-talk between adjacent test regions of the test sheet of fabric.

Hence in the absence of an integral seal (and/or other sealing arrangement), the degree of cross-talk between adjacent wells may vary depending on the type of fabric (porosity, weave, compressibility, wettability, roughness, etc.), the degree of inter-well compression (e.g., effected in the described embodiment by matched sets of raised ridges between adjacent wells), and/or the filling protocols for adjacently-situated wells (e.g., slow sequential (serial) filling versus rapid-serial filling versus substantially simultaneous (parallel) filling). A skilled artisan can, based on the guidance provided herein, including for example, reference to the various examples, determine whether a seal of any type, and in particular an integral seal, is advantageous with respect to the particular application involved, or alternatively, whether a particular application can employ a test sheet of fabric without having a seal and/or without having an integral seal. In applications where the isolation of regions of the test sheet of fabric is suitable without integral seals, the use of the inventive apparatus together with one or more test sheets lacking integral seals can result in reduced costs and complexity in preparing the fabrics, while still providing for meaningful experimental data for screening materials as described herein, and without departing from the spirit of the invention.

Although the number of the plurality of test regions 68 can vary, the methods and apparatus described herein are particularly advantageous in connection with higher throughput parallel experiments. Hence, the number preferably of test regions is preferably at least 4, 8, 15, 24, 40, 60, 90, 100, 200, 400, 500, 1000, 2000, 4,000, 10,000 or more. In preferred embodiments, # of test regions=96*N, where N is an integer ranging from 1 to 100, preferably 1–10, and more preferably 1–5. The size, planar density, and/or geometrical arrangement of the test regions are not narrowly critical, and can vary as described above in connection with the apparatus.

The test fluid may generally comprise elements, compounds or compositions, and can typically include, without limitation, polymers, surfactants, dyes, bleaches, perfumes, buffers, electrolytes, builders, sequestering agents, flame retardants, and/or enzymes, alone or in various combinations and permutations. The test fluid is preferably a liquid test fluid (e.g., solution, dispersion and/or emulsion), but can also include gaseous test fluids. In the test-fluid varying embodiment described above, two or more test fluids can differ from each other in terms of overall concentration, in terms of chemical composition, or in terms of other chemical or physical properties (viscosity, polymer molecular weight distribution, phase differences, acidity, etc.). Differences in chemical composition can be based, for example, on the presence of differing components or on the presence of differing ratios of the same components. Differences in test fluids can also be based on differences in their respective synthesis protocols, without actual characterization of the resulting test fluids. In an exemplary, non-limiting application, the test fluids can comprise one or more polymers or polymer components. The polymers or polymer components can differ with respect to composition, hydrophilicity, hydrophobicity, dipolar characteristics, charge, hydrogen-bonding characteristics, molecular weight and/or molecular weight distribution. In preferred applications, the test fluids are fabric care compositions or potential fabric care compositions being evaluated with respect to the fabric property of interest.

The fabric composition of the test sheet of fabric 64 at each of the plurality of test regions 68 may comprise the untreated fabric alone (by itself), as well as the fabric in combination with various treatment agents (e.g. coatings, adsorbed moieties, bonded moieties (e.g., covalently bonded moieties, ionically bonded moieties)), etc.). Typically, treatment agents can be employed in a fabric composition to effect a change in one or more properties of the particular fabric, including without limitation, color fastness, polymer adsorption, soil release, stain release, dye retention, dye transfer, soil redeposition, abrasion resistance, fiber building, wrinkle reduction or prevention, static reduction or prevention, and texture. As such, in the fabric-composition varying embodiment of the invention, the plurality of test regions 68 may comprise different fabric care compositions, where the compositions differ with respect to the underlying fabric material and/or the treatment agents in each of the plurality of regions, such that variations exist in the one or more aforementioned properties of the fabric.

A treated fabric array suitable for use in the fabric-composition varying embodiment as a test sheet of fabric 64 comprising a plurality of different fabric compositions at a plurality of test regions can be prepared according to any suitable method known in the art. Such a treated fabric array is preferably prepared, however, by the following method, and most preferably, by the following method using the apparatus described herein. Specifically, a plurality of test regions 68 of a common test sheet of fabric are simultaneously contacted with a plurality of treatment fluids, where the plurality of treatment fluids differ between the plurality of test regions. One or more components of the plurality of treatment fluids is allowed to interact with the test sheet of fabric at the plurality of test regions to form different fabric compositions at the plurality of test regions.

The plurality of treatment fluids for preparing a treated fabric array can, in an exemplary, non-limiting approach, comprise a polymer component that interacts with the test region of the test sheet of fabric. The polymer component can vary between the different treatment fluids with respect to composition, hydrophilicity, hydrophobicity, dipolar characteristics, charge, hydrogen-bonding characteristics, molecular weight, or molecular weight distribution, and/or other properties, such that different fabric compositions are formed on the test sheet of fabric, with each fabric composition having a different one or more polymers adsorbed onto the test region. The plurality of treatment fluids can also vary, additionally or alternatively, with respect to other types of components. In general, the plurality of treatment fluids for preparing the treated array can differ with respect to concentration, chemical composition, or other chemical or physical properties. Differences in chemical composition can be based, for example, on the presence of differing components or on the presence of differing ratios of the same components. Differences in treatment fluids can be characterized by differences in their respective synthesis protocols, without actual characterization of the resulting fluids. The resulting treated fabric array can, therefore, comprise a plurality of test regions that differ with respect to the composition of the test sheet of fabric at each region.

The property of interest being evaluated with respect to fabric care—referred to herein as a fabric property of interest—may be a property of the fabric itself, the fabric composition (e.g., treated fabric) and/or a property of the test fluid. The particular fabric property of interest is not narrowly critical to the invention, and can vary, depending on the goals of the research purpose. In general, the fabric property of interest is a fabric property that has commercial significance. As such, the fabric property of interest can be any property that affects one of the senses (e.g., look, feel, scent, sound, taste) of the end-user of the fabric, or at least a perception of one of the senses. Exemplary non-limiting fabric properties that are currently of interest include without limitation, color fastness, polymer adsorption, bonding (e.g., ionic or covalent bonding of a particular moiety), soil release, stain release, dye retention, dye transfer, soil redeposition, abrasion resistance, fiber building, wrinkle reduction or prevention, static reduction or prevention, texture, friction (or lack thereof), strength, pilling, static electricity, or other optical, chemical, electrical or mechanical properties.

Fabric properties of interest can generally be measured or determined according to methods known in the art. The methods can be applied in a serial (e.g., rapid serial) and/or simultaneous (i.e., parallel) fashion. In preferred embodiments, the plurality of test regions are simultaneously screened for the fabric property of interest, such that the relative efficacy of the variable aspect of the experiment (e.g., of different test fluids, of different fabric-compositions, of different process conditions) can be evaluated in a single screening experiment (i.e., evaluated in parallel). Exemplary techniques that will find applications with respect to determining fabric properties of interest include spectroscopic techniques (e.g., absorbance techniques, reflectance techniques, etc.), imaging techniques (e.g., digital camera), and mechanical property probing techniques (e.g., probing for puncture strength), among others.

Particularly preferred properties of interest with respect to fabric care, as well as approaches for determining certain of such fabric properties of interest are described above (e.g., color care), and/or in the following paragraphs. Such approaches are, in general, disclosed in connection with the apparatus disclosed herein. Except as specifically recited in the claims, however, such reference to the particular apparatus of the invention should be considered exemplary and non-limiting.

Component (e.g., Polymer) Adsorption. A preferred fabric property of interest with respect to the present invention is the adsorption of a component of a fabric-care composition (e.g., a polymer component) to a fabric. In order for an active ingredient in a detergent formulation to have a strong effect, it is sometimes desirable or necessary for the ingredient to be adsorbed to the surface of the fabric. This can be accomplished either if the active ingredient itself has a favorable binding interaction with the fabric surface, or if the active ingredient is chemically or physically attached to a second ingredient (e.g., a polymer) which has such an interaction. Accordingly, in many cases it is desirable to be able to determine whether or not a given chemical or substance tends to adsorb to a fabric surface. A variety of methods are generally known to those skilled in the art; many of these methods can be combined with the apparatus of the present invention to produce a test for adsorption which is parallel in nature and can be used to test many substances at once.

Tests for adsorption of a substance, and typically and preferably a dissolved substance, to a surface can function in two ways. A change in some property of the fabric may be detected following adsorption, indicative of the presence of materials on the fabric which were not present prior to exposure to the solution; or a change in the solution properties may be measured, due to a reduction in the amount of the dissolved substance (since some if it has been deposited on the fabric). Which type of method is preferable will depend on the specific substance and substrate, and on which types of physical or chemical analytical techniques can be applied to detect the above mentioned changes.

Within the context of the present invention, one skilled in the art may appreciate that almost any conventional method for detecting adsorption can be applied with the present invention. Generally, for example, an array of solutions can be prepared, containing either different dissolved substances to be tested in each well, or the same substance formulated in different ways, or some combination of the two. A clean test sheet of fabric (or fabric array) sample is also prepared. The chosen physical/chemical measurement can be made either on the clean fabric or on the array of solutions, prior to exposure of the solutions to the fabric. Then the fabric is placed in the inventive apparatus, and the array of solutions are placed in the wells in the upper plate. The pumping action of the membrane is used to flow the liquids back and forth through the fabric squares for some amount of time. Subsequently, either the liquids or the fabric or both may be analyzed again, to detect changes indicative of adsorption of the dissolved substances to the fabric. The liquids may either be analyzed directly in/from the microwasher plate, or may be removed to a separate plate for analysis. For analysis of the fabric, one will in general remove the fabric from the apparatus and rinse it to remove any of the substance which is not actually bound to the fabric surface. The fabric may then be dried, and an analysis done on the fabric to detect any adsorbed substance.

The following paragraphs illustrate several exemplary, and specific embodiments of the above described methods as applied to determination of polymer adsorption. It should be appreciated, however, by one of skill in the art, that other protocols may also be applied. The invention as disclosed herein provides a general platform which allows almost any such test to be advantageously effected, and preferably in a parallel fashion.

Many polymers contain features in their optical spectra (UV/visible/IR) which allow them to be identified. Alternatively, fluorescent moieties or dyes may be incorporated into a polymer ("tagging") in a number of ways, such as: incorporation of trace amounts of a tagged monomer into the polymer backbone; tagging of the initiator, or of terminating or chain-transfer agents; or reaction of a tag with a polymer after synthesis. The concentration of the polymer in solution, before and after exposure to the fabric, may then be measured spectroscopically, and the reduction in concentration due to adsorption to the fabric may be determined. Alternatively, a spectroscopic or other optical assay may be applied to the fabric before and after exposure to the solution. A specific example: if a polymer incorporates a fluorescent moiety, then fluorescence may be detected in the array of test solutions before and after exposure to the fabric; or the fabric itself may be scanned for fluorescence before and after exposure to the test solutions.

In some cases, it may be necessary or desirable to carry out a chemical reaction or other chemical interaction (other than making or breaking covalent bonds) on the dissolved substances in order to manifest their presence more easily. In general, a moiety of interest (e.g., the adsorbed moiety) may be reacted with a detection agent to form a detectable species, and the detectable species may then be detected (e.g., with visual, spectroscopic or other optical methods as described). For example, a dissolved substance (e.g., polymer) to be determined may be reacted with a detection agent to result in a color change of the solution, with an absorbance maximum at a particular known wavelength. The strength of the absorbance can be proportional to the concentration of the substance being determined.

The concentration of a polymer and changes therein may also be determined by viscosity measurements, since viscosity increases with concentration of polymer. Methods for rapid measurement of viscosity on arrays of solutions have been described in the art, both with respect to parallel and/or serial approaches, including for example, in co-pending application filed May 26, 2000 by Hadjuk et al., Ser. No. 09/580,024 entitled "Instrument for High-Throughput Measurement of Material Physical Properties and Method of Using Same."

Polymer concentration may also be determined through chromatography—samples of the solutions before and after exposure to the fabric are analyzed using any of a number of standard techniques, and the peak area corresponding to the substance of interest can be integrated to give a number proportional to the concentration before and after exposure to the fabric. Methods for high speed chromatography have been described in the art, including for example in PCT patent application WO 99/51980 entitled "Rapid Characterization of Polymers".

The wetting behavior of a drop of liquid deposited on the treated fabric can also be used as a measure for ingredient (e.g., component) adsorption. If the fabric surface has been modified by adsorption of a material from a solution or dispersion or emulsion, then the behavior of a drop of liquid which is deposited on the fabric can be different depending on the degree of adsorption. The drop may either bead up or be absorbed/spread by the fabric in a different fashion. The extent of wetting behavior can be calibrated through known methods with the particular degree of adsorption.

Detergency. In order to test the efficiency of different detergent formulations on removing soils or stains, the following general method may be applied. A fabric array is first stained with a particular type of soil, in as uniform a manner as possible. For example the soil may be applied by immersing the entire fabric in a solution and letting it dry. Uniformity can be improved by passing the wet fabric through a pair of rollers, to remove excess staining solution. Alternatively, the stain may be applied by brushing on the staining solution and letting it dry; by deposition from an automated pipette with one or more tips; or by using a pin transfer tool, which is first dipped in the staining solution and then dabbed on the fabric. Or the fabric may be placed in a container with particulate soils and shaken. The stained fabric can then be imaged by any of a number of means— with a camera (e.g., a digital camera, CCD camera, etc.), a flatbed scanner, or a scanning reflectance probe of some type. The data are preferably stored for use later in a comparative step.

Then the stained fabric array can then be placed in the inventive apparatus. A different solution can be placed in each well, for example containing different types of surfactants, bleaches, enzymes, etc. The solutions are forced back and forth through the fabric for a set time. Then the liquids are removed, and the fabric is removed, rinsed, dried, and imaged. A comparison of the images of the fabric from before and after washing allows for a measurement of the degree to which the soils have been removed by the different detergent formulations.

Optionally, a clean fabric array may be placed in the apparatus together with the soiled one, in order to determine the degree of soil redeposition or soil transfer from the dirty fabric to the clean one.

Soil Release Due to Adsorption/Pretreatment. A known polymer (Gerol, manufactured by Rhodia) helps remove soils from synthetic (polyester) fibers in that the polymer is deposited on the clean fabric during an initial washing. Soil which is subsequently deposited on the fabric is in contact with this adsorbed polymer layer, not with the fiber itself. When the soiled fabric is then washed again, the polymer layer has the effect of aiding in the release of the soil, even if the polymer was only present in the initial wash.

Polymers may be tested for this type of soil release mechanism and behavior using the inventive apparatus. A clean fabric array is installed in the apparatus. An array of solutions containing test polymers is placed in the array, and flowed through the fabric for some time to allow for the polymers to adsorb to the surface. The liquids and fabric are removed, and tested to detect adsorption of the polymer if desired. The fabric is then stained; imaged in the stained condition; washed; and imaged again, to gauge the effectiveness of the adsorbed polymers (if any) on the release of subsequently deposited soils. Because the polymer has its effect due to being adsorbed during the initial washing step, not the final soil removal washing step, the final step may be done with more conventional apparatus—i.e. the entire fabric may be washed in a single vessel for the final soil removal step.

Color Testing. In many cases it is desirable to test the effect of a fabric care composition on the appearance of a fabric, specifically on the color. Specific effects which are of interest include color loss from a fabric, and transfer or bleeding of color from one fabric to another. These effects may be studied or tested in the inventive apparatus using the following methods. Generally at least two pieces of fabric will be installed in the apparatus. One fabric will generally be dyed or colored, and the other is not dyed or white.

A plurality of differing liquid compositions are placed in the different wells, corresponding to the different fabric regions. The liquid is made to circulate, preferably simultaneously, over and/or through the fabrics at each region, either by use of a flexible membrane as described earlier, or by some other method of agitation, in order to insure that the fluid is in intimate contact with both fabrics. After a specified time has passed, the liquid samples may be removed from the apparatus, for example using an 8-, 12-, or 96-tip pipetting apparatus, and placed in a separate microtiter plate for analysis. The remaining liquid in the apparatus is then poured out, and the wells and fabric regions are rinsed several times with clean water to remove any remaining colored liquid. Then the fabrics are removed from the apparatus and dried.

One or more of the fabric which was initially colored, the fabric which was initially white, and/or the liquids removed from the wells may then be analyzed to detect color changes. Each, or only one or two of these objects may be analyzed. For example, the fabric samples may be analyzed using for example a scanning reflectance spectrophotometer or a color imaging device such as a camera or scanner, and the liquid samples may be analyzed by a camera or a UV-vis spectrophotometer which is designed to handle 96 well plates (such as the Spectramax, manufactured by Molecular Devices).

One can observe the following types of effects: color loss or color change in the originally colored fabric; color change due to dye pickup on the white fabric; and color change in the liquid due to dye which remains dissolved and does not deposit on the white fabric. For example, one may in this manner distinguish between compositions which prevent dye loss from the colored fabric, and compositions which do not inhibit such loss but do prevent the dye from redepositing on the white fabric. These two cases are distinguished by the absence or presence, respectively, of color in the wash liquid.

There are many other configurations of fabrics and test procedures which can be used with the inventive apparatus for such appearance-based tests, as will be obvious to one skilled in the art. For example, if only color loss is to be studied and one is not interested in dye transfer (i.e. one is testing only for colorfastness), the white "pickup" cloth may be omitted, and the results assessed only from the color of the fabric sample after treatment, possibly augmented by an analysis of the liquid. As another example, the behavior of several different dyes or combinations of dyes may be analyzed simultaneously, either by including several pieces of fabrics containing different dyes, or a single piece of fabric dyed with multiple dye types. By colorimetric analysis of the fabric, the extent of bleeding of the different dye species may be determined more rapidly than would be possible using a separate experiment for each dye type. In yet other examples, the inventive apparatus may also be employed to test new types of molecules intended for use as dyes, either to determine the color when applied to a fabric, or the extent of binding of the dye to a given type of fabric. It may also be used to test the conditions under which such dying is done, i.e. the formulation from which the dye is delivered, which may contain such variables as ionic strength and pH, as well as to test the use of auxiliary substances such as dye fixers which aid in promoting strong binding of the dyes to the fabric.

Other specific screens for these and other specific properties of interest with respect to fabric care are known in the art, and or may be developed in the future. Advantageously, such screening approaches and protocols can be adapted for use in connection with the apparatus and methods disclosed and claimed herein.

The apparatus may also be used for applications other than those described herein. For example, the apparatus shown in FIGS. 1A, 1B, and 1C maybe used as a parallel micro pump. Pressure can be created by installing inlet check valves into inlet passages in fluid communication with the fluid chambers and outlet check valves into outlet passages in fluid communication with the fluid chambers. When a vacuum is applied to the cavities the inlet check valves open and the fluid chambers are filled with fluid. When pressure is applied to the cavities, fluid within the chambers is pressurized and forced through the outlet check valves.

The apparatus may also be used as a parallel reactor for evaluating catalysts, and especially for evaluating heterogeneous catalyst candidates. In such applications, plurality of heterogeneous catalysts (or catalyst precursors) having different compositions can be incorporated into the apparatus such that the plurality of catalyst candidates are simultaneously contacted with a reactant-containing fluid. The catalyst materials can be bulk, or supported catalyst materials. The catalyst materials are preferably incorporated into the apparatus as part of the porous sheet 64 (e.g., with catalyst materials at, on or in the test regions 68 of the porous sheet). In a particularly preferred approach, the porous sheet 64 (or at least the test regions thereof) can act as a porous support for the catalytically-active materials. For example, the catalyst candidates (or catalyst precursors) can be impregnated into the test regions of the porous sheet, calcined, and then integrated into the parallel reactor. The catalyst materials can also be deposited at, on or into the plurality of fluid chambers 54, for example, loosely, fixedly, formed as a film, contained within one or more frits or other retaining mesh). The catalyst materials can, in a further approach, be formed at, on or in the flexible membrane. In any format, each of the plurality of candidate catalysts are preferably, provided in discrete, separate test regions to avoid cross-talk between catalysts, and to provide for spatial deconvolution of catalyst performance. The pressure-induced agitation of the present invention can improve the contact and mass transfer between the reactant-containing fluid and the heterogeneous catalyst. The parallel reactor 20, 84, 150 is preferably configured as a parallel batch or semicontinuous reactor, and in some embodiments, could also be configured as a parallel continuous-flow reactor.

The following examples illustrate the principles and advantages of the invention.

EXAMPLE 1

Preparation of Fabric Library Substrates with Integral Seal

The ink used for screen printing was a black Ultrasoft Plastisol from Union Ink Company (453 Broad Avenue, Ridgefield, N.J., 07657). The ink was diluted by adding approximately 30% reducing solution to reduce the viscosity and facilitate penetration of the ink through the pore spaces and mesh of the cotton fabric. A 156 mesh screen was used in printing, again to facilitate a high degree of ink flow into the fabric. The fabrics used were woven cotton fabrics. Immediately after printing, the ink was cured at about 230° C. for approximately 15 seconds. It was found empirically that a shrinkage of approximately 1% occurred during the curing process; therefore the screen pattern was fabricated at a scale of 101%, so that the final pattern after curing corresponded closely to the desired 9.0 mm pitch.

The final step in preparation of the fabric samples was die cutting of the fabrics. This produced a sample which fit completely within a microtiter plate footprint (with no "overhang"), and which was punched for adaptation with respect to each of the following: pin holes for alignment with the apparatus; through holes or spaces for passage of the screws used in assembly; and a cut-out on one corner to allow for unambiguous definition of the orientation of the library and the identity of cell (e.g., row 1, column 1).

EXAMPLE 2

Isolation Between Wells

Testing for the confinement of liquid to the individual cells (isolation) was effected by installing and sealing the test sheet, filling selected wells with a colored liquid, agitating, and then observing whether any wicking or diffusion of the liquid to an adjacent cell occurred. Such "crosstalk" was assessed using test sheets of woven cotton fabric having screen-printed integral seals, as well as with plain (unprinted) test sheets of fabric of the same material, but without the screen-printed integral seals.

The experimental conditions were controlled to evaluate two types of forces that could impact the degree of crosstalk between wells—capillary forces (e.g., wicking) and diffusion forces. As demonstrated below, the distinction between the types of forces with respect to crosstalk was particularly evident in connection with the plain, unprinted test sheets of fabric (lacking an integral seal). As such, the forces discussed herein are particularly relevant in connection with such plain, unprinted test sheets of fabric. In one set of experiments, capillary forces (wicking) were examined in the context of a first well containing liquid adjacent to a second empty well; in that case, it was postulated, based on observed results disclosed below, that capillary forces would provide a strong driving force to pull the liquid into the empty neighboring well, where the fabric is dry. Such a condition could occur during research, for example, if a plate would be filled using a single-tip, 8-tip, or 12-tip liquid dispenser, wherein some wells would be filled before others; or if an experiment would be performed in which the contact time between liquid and fabric is a variable, such that some wells are intentionally filled before others. In a second set of experiments performed to examine isolation between adjacent wells, diffusion forces were examined in the context of two neighboring wells that both contained substantially similar liquids, and that differed only in the composition and/or concentration of a dissolved species; in such cases, it was postulated, based on observed results disclosed below, that capillary forces would be substantially absent and that the transport of the dissolved species between wells would occur, if at all, primarily by diffusion (rather than by capillary flow or wicking of the solvent and solute).

The colored liquid used in each of the tests was a solution of the dye Direct Yellow 4 (CAS number 3051-11-4, available from Aldrich (Milwaukee, Wis.)) at a concentration of 0.5 mg/ml in demineralized water. The clear liquid used in each of the tests was demineralized water. The volume of liquid in each well was 400 $\mu$l in all cases. Isolation was evaluated under four different sets of experimental conditions, summarized as follows:

Experiment IA: no integral seal; all wells either contained colored liquid or left empty.

Experiment IB: integral seal; all wells either contained colored liquid or left empty.

Experiment IIA: no integral seal; all wells contained either colored or clear liquid.

Experiment IIB: integral seal; all wells contained either colored or clear liquid.

As noted above, the conditions of Experiments IA and IB tested isolation under conditions where capillary forces were deemed to be more important, whereas the conditions of Experiments IIA and IIB tested isolation under conditions where capillary forces were postulated as being substantially absent and where diffusion was deemed to dominate the transport of liquid or dissolved species between wells.

A microwasher apparatus was assembled in each of the Experiments IA, IB, IIA and IIB as follows. First, a single piece of a flexible, latex membrane was first installed directly adjacent to the base plate and adjacent to the cavities which were in communication with the source of controlled pressure. The flexible latex membrane was 0.006" thick "Natural Latex Sheeting" from the Hygenic Corporation (part #08535). Then, for each of the experiments, three test sheets of fabric were installed on top of the membrane and adjacent to each other—with each of the three test sheets in a given experiment either having or lacking the integral seal (depending on the experiment as outlined above).

For Experiments IA and IB, the colored liquid was dispensed in serial fashion directly to the selected wells of the assembled microwasher apparatus by a liquid handling robot, with other remaining cells left empty. For Experiments IIA and IIB, the colored liquid and clear liquid were first dispensed into selected wells of a 2 ml polypropylene microtiter plate, and were subsequently transferred substantially simultaneously to the loaded microwasher apparatus with an automated 96-tip pipette. The substantially simultaneous transfer was effected in order to minimize, and preferably substantially avoid capillary flow during filling. Once the plates were filled, they were placed on the base station and pneumatically actuated for one hour, using a pressure differential of 3 psi and 7 inches Hg vacuum and a cycle time of 0.5 seconds per complete cycle. An exception to this general protocol was made in connection with Experiment IA, where within five minutes after filling the wells and beginning agitation, significant wicking of the colored liquid to neighboring cells was already apparent, and the experiment was stopped after only ten minutes to avoid ending the experiment with a completely uniform coloring of the fabric, and to therefore preserve some vestige of the initial pattern of cells filled with colored and clear liquids.

When agitation was complete, the remaining liquid was poured out, and the empty microwasher plates were placed in a convection oven at 50° C. for six hours, until the fabric was completely dry. Such drying was done to minimize colored liquid flow between cells when the apparatus was disassembled and the constraints preventing flow were released. In principle, such drying could be accelerated, for example, using the flexible membrane and pneumatic connection to provide convective flow air back and forth through the damp fabrics.

FIGS. 8–11 show the results of these experiments. The images of the fabrics were acquired using a Hewlett-Packard ScanJet 6200C flatbed scanner.

The image from Experiment IA (FIG. 8) shows that the colored liquid readily wicked from one cell to the next in less than 10 minutes in the triple-stacked test sheet configuration, where each of the three test sheets lacked an integral seal.

In contrast, the image from Experiment IB (FIG. 9) demonstrates that the integral seals in each of the test sheets completely prevented wicking from occurring in the triple-stacked test sheet configuration—even over a one hour time period.

Moreover, the image from Experiment IIA (FIG. 10), shows that fairly good isolation between wells can be obtained with the inventive apparatus using triple-stacked test fabrics, even without an integral seal, where the wells are filled substantially simultaneously or in rapid serial fashion, such that a filled well is not adjacent to an empty well for a period of time sufficient to cause undesired wicking and associated cross-talk between adjacent regions of the test sheet of fabric. (Compare Experiment IA). The actual time that adjacent empty and filled wells can coexist will vary depending on several factors, including fabric properties, test fluid properties, and the particular apparatus employed in the screening, each of which is discussed further below. It is noted in this regard, that the partial wicking shown in FIG. 10 for the sample of Experiment IIA (without the integral seal) occurred predominantly during the drying stage; such partial wicking was observed to be substantially absent immediately after the one hour liquid exposure. Without being bound by theory not specifically recited in the claims, the effectiveness of Experiment IIA (configured with triple-stacked test sheets, each without an integral seal) was attributed to the raised ridges between each of the wells on both the top and bottom plates, which focus the pressure applied by the screws onto very narrow regions, such that the fabric in these regions is strongly compressed between each of the adjacent regions. The inter-well compression of the test sheets of fabric greatly reduces the pore space available and thus serves to greatly slow down the diffusion of liquid from one cell to the next by reducing the effective cross section of the pores available for diffusion. Hence, Experiment IIA demonstrates that when such inter-well compression is combined with the substantially simultaneous filling of adjacent wells (or sufficiently rapid serial filling of adjacent wells)—thereby minimizing and preferably substantially avoiding capillary forces (e.g. wicking) as the cross-talk mechanism—favorable results are achieved with respect to isolation of individual regions of the test sheet(s) of fabric.

The image from Experiment IIB (FIG. 11) demonstrates that the integral seals in each of the triple-stacked test sheets also completely prevented diffusion from occurring in the triple-stacked test sheet configuration over the one hour test period.

In summary, based on the results of Experiments IB and IIB (considered alone and/or in combination), the integral seal has been demonstrated to effect substantially complete isolation between the wells, and therefore, between adjacent regions of the test sheets of fabric, over long time scales. In the absence of an integral seal, results may vary depending on the type of fabric (porosity, weave, compressibility, wettability, roughness, etc.), the degree of inter-well compression (e.g., effected in the embodiment of this example by matched sets of raised ridges between adjacent wells), and/or the filling protocols for adjacently-situated wells (e.g., very slow sequential (serial) filling versus substantially simultaneous (parallel) filling or sufficiently rapid-serial filling). Hence, in applications where it is desirable or necessary to fill some adjacent wells at different times than other adjacent wells, rather than simultaneously, the use of an integral seal and its associated superior isolation under a broader range of conditions presents definite advantages. In applications where the isolation of regions of the test sheet of fabric is suitable without integral seals, however, use of the inventive apparatus together with one or more test sheets lacking integral seals can result in reduced costs and complexity in preparing the fabrics, while still providing for meaningful experimental data for screening materials as described herein, and without departing from the spirit of the invention.

EXAMPLE 3

Effect of Different Dissolved Substances on Dye Loss and Transfer

The materials used in this example are summarized as follows:

Poly(vinylpyrrolidone), Mw=55,000 (Aldrich, cat. #85, 656-8), abbreviated as PVP; Poly(vinylpyridine N-oxide), Mw=200,000 (Polysciences, cat #23684), abbreviated as PVP-N-O; Sandofix SWE Liquid (cationic dye fixer, Clariant product #260802), abbreviated as SWE; Sodium dodecyl sulfate (Aldrich 86,201-0), abbreviated as SDS.

A library of different test fluids was prepared from the starting materials and demineralized water as follows. 100 mg of each material was dissolved in 20 ml of demineralized water and agitated until fully dissolved. A formulation library was designed using Library Studio™ graphical library-design software (available from Symyx Technologies, Inc., Santa Clara, Calif.). The design of the library, in table format, is shown in Table I (FIG. 12), where: the numbers in the table represent the mass fraction of each ingredient in the formulation recipe, in parts per million (ppm), with the remaining mass being demineralized water. The various materials and/or various amounts of materials for each of the different test fluids formulations were dispensed into wells in micro-titer format using a single-arm/single-tip liquid dispensing robot, controlled by Impressionist™ instrument-control software (available from Symyx Technologies, Inc., Santa Clara, Calif.). Specifically, 2 ml of each solution were formulated in the wells of a 2 ml polypropylene microtiter plate, by dispensing appropriate amounts of the polymer and surfactant stock solutions and bringing the volume up to 2 ml with plain demineralized water. The formulations were well mixed by sealing the top of the microtiter plate and shaking.

Referring further to Table I (FIG. 12), in the first three rows, only water and one polymer were present in each well. The concentration of each polymer increased across each row from zero to 100 ppm in substantially equal steps. In the fourth row, only water and surfactant were present, and the concentration increased linearly from zero to 1000 ppm. These numbers were chosen to be typical of the concentrations used for polymers and surfactants, respectively, in laundry detergent formulations. In rows five through seven, each well contained a single polymer as well as anionic surfactant. The polymer concentration was fixed at 100 ppm, while the surfactant concentration increased from zero to 1000 ppm. Finally, in row eight two different polymers were present without surfactant. The total polymer concentration was fixed at 100 ppm, but the relative proportions of the two polymers varied across the row.

The test fluids comprising the formulations contained in the library were then screened with respect to dye transfer properties. A microwasher bottom plate was loaded as follows: a latex membrane was installed first, closest to the cavities in the bottom plate. On top of the membrane were placed a red dyed fabric and a white fabric, in that order. The red fabric had been uniformly dyed with red dye #80 (particular method of dying and total dye loading not known), and no dye fixers were used during or after dyeing. Both the red and white fabrics had previously been screen printed with an integral seal pattern as described in Example 1. 400 $\mu$l of the formulation library was transferred from the 2 ml plate to the wells of the microwasher plate using a 96-tip robotic pipetting station (Cyberlab A400). Immediately after transfer the microwasher plate was placed in the heated docking station (40° C.) and the pneumatic agitation was then turned on to agitate the uncovered microwasher assembly. The duration of agitation was 30 minutes. When agitation was completed, the microwasher was removed from the docking station and 200 $\mu$l of the wash liquid was transferred to a clear plastic microtiter plate using the 96-tip pipette. The remaining liquid was poured out and the block was rinsed several times with clean water, to remove excess colored liquid. The fabrics were then removed from the microwasher and allowed to air dry.

Figure 13A:
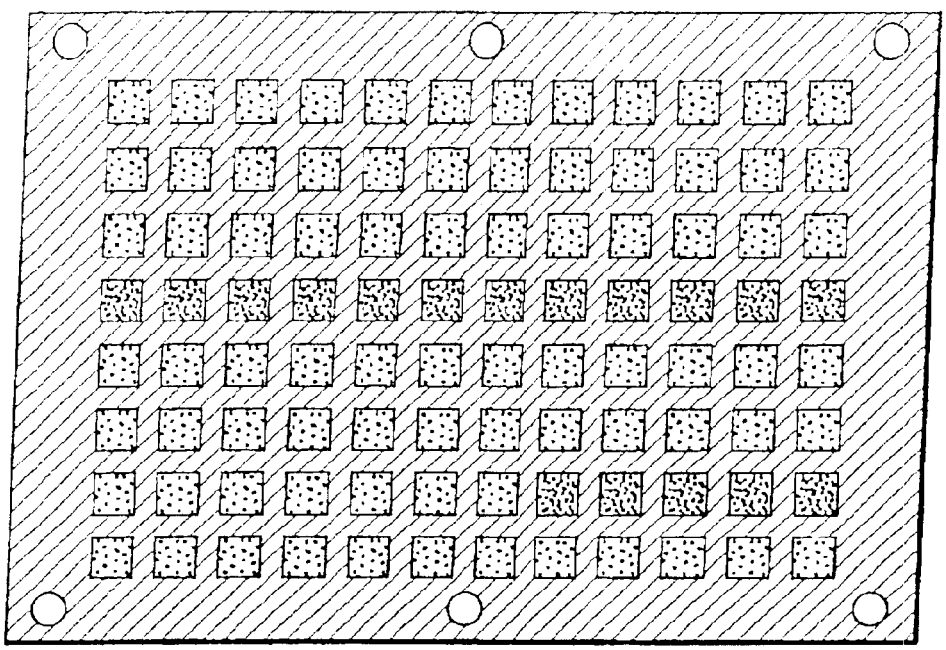
FIG. 13A is a plan view of a test sheet used in testing the libraries listed in FIG. 12.

An image of the white fabric (with transferred dye) was then recorded using a Hewlett Packard ScanJet 6200C flatbed scanner, and is shown in FIG. 13A. The brightness, contrast, and gamma settings were set to values (255/0/1) which had been previously shown to produce an approximately linear response to the reflectance of neutral density gray scale targets on a GretagMacbeth Color Checker chart. The recorded image was a 32-bit full color image (256 possible color values each for Red, Green, and Blue, per pixel) and was recorded at 150 pixels per inch resolution. This was sufficient to resolve the individual threads in the fabric without aliasing effects due to the interplay of the thread spacing and pixel spacing, which occur if the image resolution is not fine enough.

An image analysis program was used to extract average red-green-blue (RGB) spectrum analysis coordinates from each square in the array. An exemplary analysis program is described in U.S. patent application Ser. No. 09/415,772, filed Oct. 8, 1999 by Crevier et al., entitled "Analysis of Chemical Data from Images." In the program, the center of each square was located automatically, a circle was defined about the center with a diameter of approximately one half the width of the square, and the RGB values of all pixels within the circle were averaged to obtain the numbers shown in Table II (FIG. 14). Rows 1–8 for each color (red, green, blue) in Table II correspond to rows 1–8 of the test regions shown in FIG. 13A. The color coordinate which is most sensitive to the presence of the particular dye used in this example was the "green" or G coordinate, where maximum light absorption occurs. The B coordinate was less sensitive, and there was almost no sensitivity in the R coordinate at all (most red light was reflected). As is well known to one skilled in the art of color analysis, various procedures may be used to calibrate the scanner's color response and convert RGB coordinates (which may be specific to a particular imaging instrument), in good approximation, to more widely used systems (which may be absolutely defined or more representative of more absolute values), such as the CIE coordinates (x,y,Y) or (L,a,b). For reference purposes, the average RGB color coordinates for a plain white fabric array from the same fabric lot and imaged with the same scanner under the same conditions were: R: 223.6+/−2.97; G: 224.4+/−2.93; and B: 217.3+/−3.48.

Figure 13B:
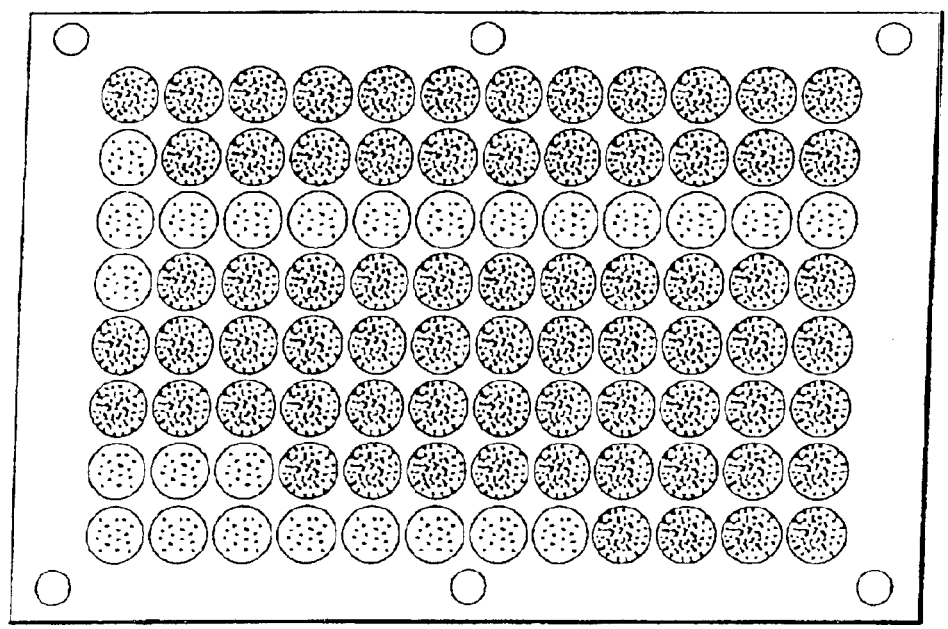
FIG. 13B is a plan view showing liquid which was in contact with test regions of the test sheet of FIG. 13A.
Figure 15:
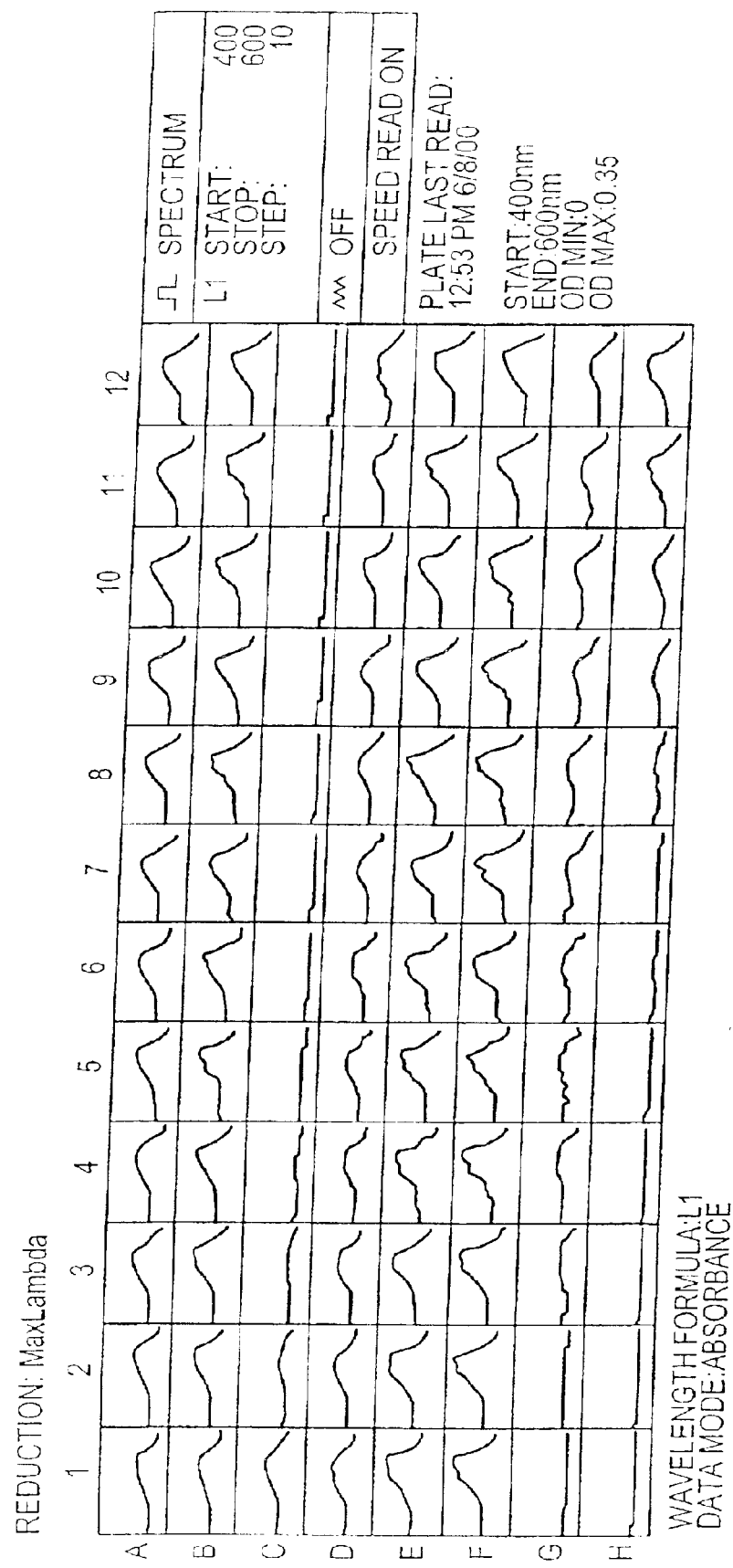
FIG. 15 is a graph showing spectra data for the liquid samples shown in FIG. 13B.

The plate containing the liquid samples was analyzed in a Spectramax spectrophotometer (Molecular Devices). Spectra were obtained over the range 400 to 600 m with 10 nm resolution, and are shown in FIG. 15. Rows A–H in FIG. 15 correspond to rows 1–8 of test samples in FIG. 13B. The plate was also photographed with a digital camera, and a gray scale image is shown in FIG. 13B. The contrast has been adjusted to bring out the color differences due to varying amounts of dye in the different solutions. The contrast in the image of the fabric was similarly adjusted for display purposes.

Regardless of the specific interpretation of the data (which will be discussed briefly below), several features are notable. Smooth variations of the fabric and liquid color are observed across the rows, but the trends within each row are distinct from those in neighboring rows. This is consistent with isolation between neighboring wells, as demonstrated in Example 2. Furthermore, cells which contain nominally identical chemical compositions yield nominally identical color results. For example, cells (1,1), (2,1), (3,1), and (4,1), (each as "row, column") all contain only demineralized water. Referring to Table I, the "green" coordinates for these cells are 145, 144, 146, and 143 respectively, well within the standard deviation of +/−3 observed for a plain white (undyed) fabric. As another example, cells (1,12), (5,1), and (8,12) contain 100 ppm of poly(vinylpyrolidone) and no surfactant. The "green" coordinates are 210, 211, and 208, respectively. Cells (2,12) and (6,1) contain 100 ppm of poly(vinyl pyridine-N-oxide) and no surfactant, and the "green" coordinates are 220 and 222. Cells (3,12) and (7,1) contain 100 ppm of the SWE fixer polymer and no surfactant, and the "green" coordinates are 213 and 205. Thus, there is a well defined relationship between the chemical composition of the liquid contained in a well, and the amount of dye transfer from the red to the white fabric.

Figure 16A:
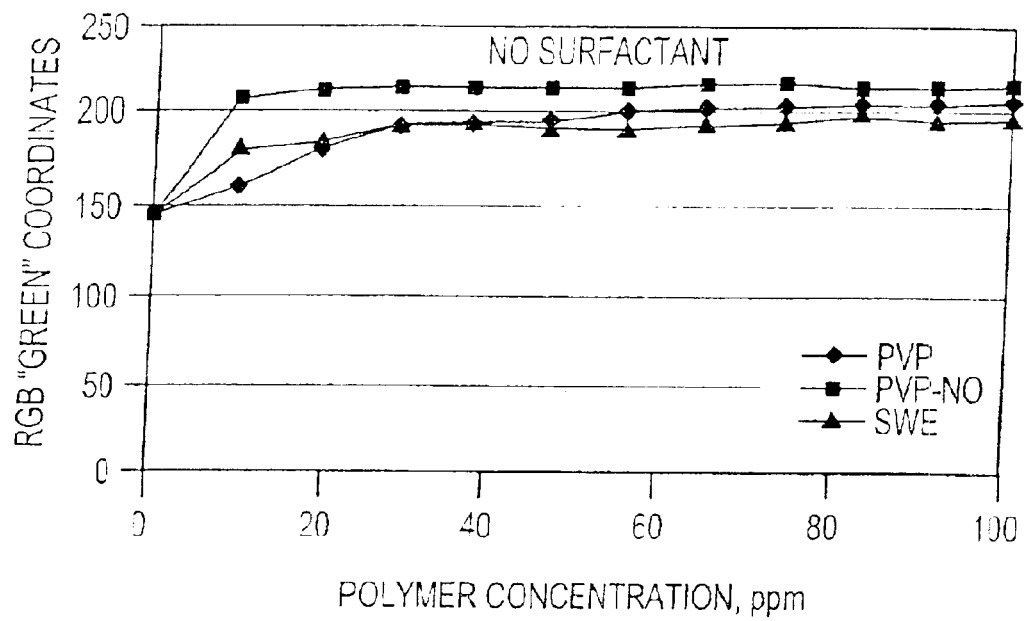
FIG. 16A is a graph illustrating the effect of polymer concentration with no surfactant.
Figure 16B:
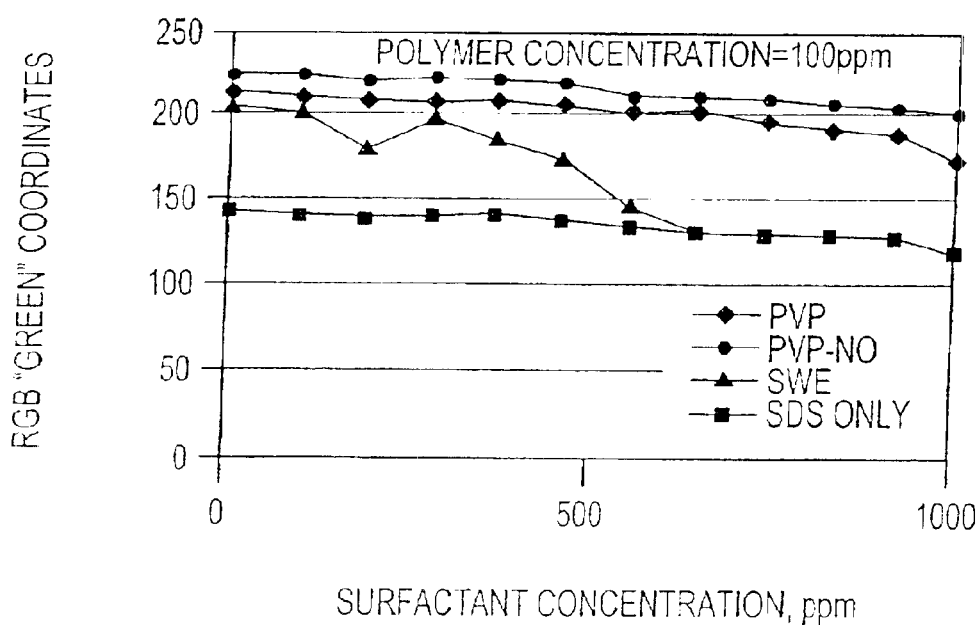
FIG. 16B is a graph illustrating the effect of surfactant concentration with polymer concentration fixed at 100 ppm.
Figure 16C:
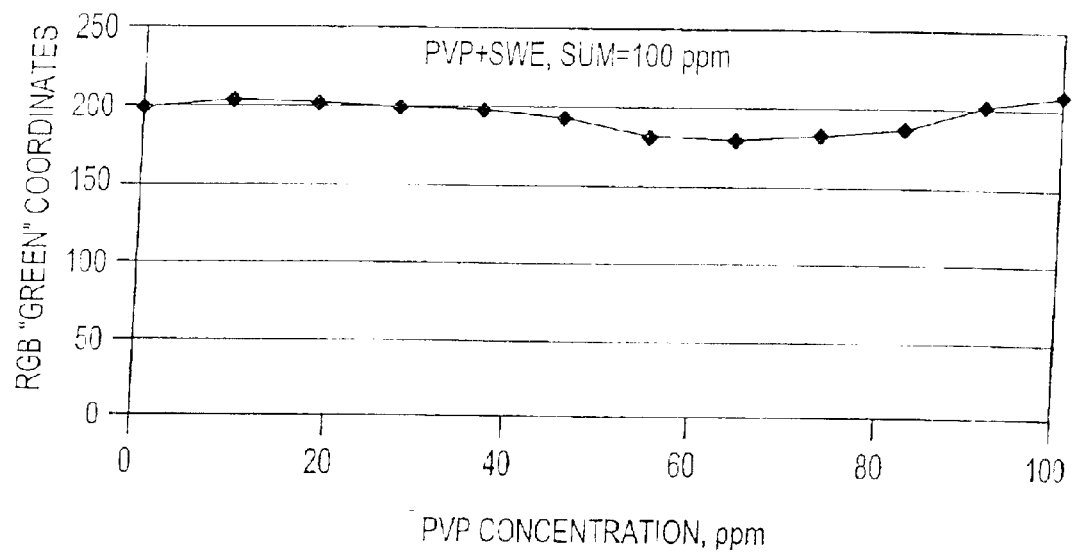
FIG. 16C is a graph illustrating fabric reflectance.
Figure 16D:
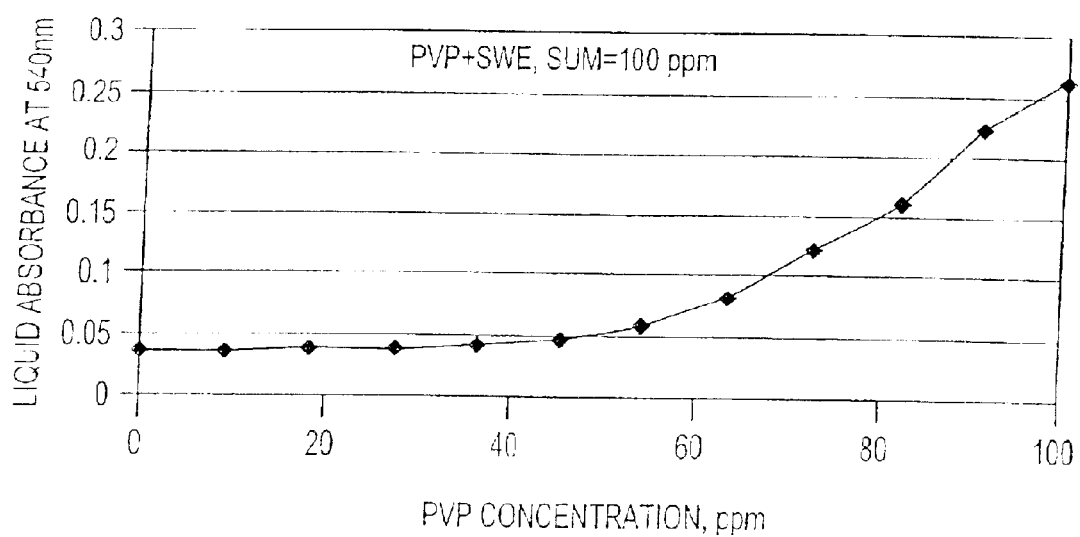
FIG. 16D is a graph illustrating liquid absorbance.

Trends observed in the library are discussed below with reference to the graphs shown in FIGS. 16A, 16B, 16C, and 16D. FIG. 16A illustrates the effect of polymer concentration with no surfactant; FIG. 16B illustrates the effect of surfactant concentration with polymer fixed at 100 ppm concentration; FIG. 16C illustrates fabric reflectance for a mixture of PVP and SWE; and FIG. 16D illustrates liquid absorbance at 540 nm wavelength for a mixture of PVP and SWE. Poly(vinylpyrolidone), abbreviated PVP, and poly (vinyl pyridine-N-oxide), abbreviated PVP-N-O, are both commonly used in laundry detergent formulations as anti dye transfer (ADT) polymers. While they do not prevent dye loss from colored fabrics, they bind or scavenge free dye in solution and prevent it from redepositing on other articles of clothing. Thus the wash liquid attains a colored appearance, but other articles of clothing largely retain their original color and do not pick up the dye which has been lost.

This is entirely consistent with the behavior observed in the experiment, wherein dye transfer is strongly inhibited by both of these polymers, but significant amounts of dye are present in the solutions, as shown by comparison of the liquid image and spectrum (FIGS. 13B and 15). In contrast, the Sandofix SWE polymer is a cationic dye fixer, which binds to both the cotton fabric and the dye molecules through charge interactions (cotton and the dye are both negatively charged, while the fixer is positively charged). Thus the fixer not only prevents dye transfer to the white fabric, but also prevents dye loss from the red fabric, as is most easily seen by looking at row 3 of the image and spectrum from liquid plate (FIGS. 13B and 15). The amount of dissolved dye is reduced as the fixer concentration is increased, opposite the behavior observed for the other polymers.

The data also permit further semi-quantitative judgements to be made. For example, PVP-N-O is readily seen to be a much more effective ADT polymer than PVP, yielding a higher ultimate brightness and having a lower threshold concentration for maximum activity. The superiority of PVP-N-O to PVP in this regard is well known to those skilled in the art of laundry detergent formulation. In fact the G coordinate of 220 for PVP-N-O is almost equal to the value of 224 measured for a new piece of undyed fabric. Also, the SWE fixer polymer yields poorer ultimate performance as judged by the color of the white fabric, even though elimination of color in the liquid is a desirable property.

Thus qualitative and semi-quantitative judgements may be rapidly made on the performance of single ingredients. Additionally, formulations may be studied using the apparatus, in which multiple components with varying ratios are present. For example, in rows 5–7, the effect of the anionic surfactant SDS on the performance of the three polymers is studied. The surfactant has only a minor effect on the performance of the PVP and PVP-N-O polymers, but substantially eliminates the beneficial effects of the SWE fixer above a surfactant concentration of about 500 ppm. This is due to the fact that the cationic polymer becomes complexed to the anionic surfactant and precipitates. It is noteworthy that above 500 ppm SDS, the data for the SWE/SDS combination coincides almost exactly with that for pure SDS.

Also, it can be seen that adding anionic surfactant to the liquid even in the absence of any polymer leads to an increase in dye transfer, in comparison to plain demineralized water. This can be seen from looking at row 4 in FIGS. 13A, 13B, and 15, the data in Table II (FIG. 14), and the corresponding graph in FIG. 16B. This occurs because the dye is charged; adding anionic surfactant increases the ionic strength of the liquid and increases the solubility of the dye, since it reduces the Debye screening length.

Finally, in row 8 a blend of PVP and SWE is studied, at fixed total polymer concentration. A smooth transition from dye fixing to anti dye transfer behavior is observed, as is seen most clearly from the image and data of the liquid samples. The best performance as judged by the fabric color occurs at the endpoints, and thus little, if anything, appears to be gained by mixing these two polymers.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

Although the present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. An apparatus for use in performing a plurality of tests in parallel, the apparatus comprising:

a first plate having openings extending at least partially therethrough to form a plurality of cavities;

a second plate having a plurality of openings extending at least partially therethrough and forming a plurality of individual fluid chambers for performing a plurality of tests in parallel;

a first sheet interposed between the first and second plates and having a plurality of porous test regions separated by a seal integral with the first sheet to prevent fluid transfer between the test regions, periphery edges of the fluid chambers being in contact with the seal, the test regions being aligned with the fluid chambers such that each of the test regions is exposed to one of the chambers; and a flexible membrane positioned between the first plate and the first sheet such that changes in pressure within the cavities cause deflection of the membrane and force fluid to pass through the porous test regions;

wherein the first sheet is held in place by a force exerted by the first and second plates when the apparatus is in an assembled configuration and removable from the first and second plates when the apparatus is in an unassembled configuration.

2. The apparatus of claim 1 further comprising a sealing sheet having openings aligned with the test regions and positioned adjacent thereto.

3. The apparatus of claim 1 wherein said fluid chambers each have a fluid volume of between approximately 0.1 milliliters and 5 milliliters.

4. The apparatus of claim 1 wherein the seal is formed from an ink material.

5. The apparatus of claim 4 wherein the ink is plastisol ink.

6. The apparatus of claim 4 wherein the ink material is heat transfer printed on the first sheet.

7. The apparatus of claim 4 wherein the ink material is silk screen printed on the first sheet.

8. An apparatus for use in performing a plurality of tests in parallel, the apparatus comprising:
- a first plate;
- a second plate having a plurality of openings extending at least partially therethrough and forming a plurality of fluid chambers;
- a third plate having openings extending at least partially therethrough to form a plurality of cavities, the second plate being positioned between the first and third plates;
- a first sheet interposed between the first and second plates and having a plurality of porous test regions separated by a seal integral with the first sheet to prevent fluid transfer between the test regions, the test regions being aligned with the fluid chambers such that each of the test regions is exposed to one of the chambers; and
- a flexible membrane sheet positioned between the second and third plates such that changes in pressure within the cavities cause deflection of the membrane and force fluid to pass through the porous test regions;
- wherein the first sheet is held in place by a force exerted by the first and second plates when the apparatus is in an assembled configuration.

9. An apparatus for use in performing a plurality of tests in parallel, the apparatus comprising:
- a first plate;
- a second plate having a plurality of openings extending at least partially therethrough and forming a plurality of fluid chambers;
- a third plate, the second plate being positioned between the first and third plates;
- a first sheet interposed between the first and second plates and having a plurality of porous test regions separated by a seal integral with the first sheet to prevent fluid transfer between the test regions, the test regions being aligned with the fluid chambers such that each of the test regions is exposed to one of the chambers; and
- a second sheet having dyed porous test regions interposed between the second and third plates and exposed to the fluid chambers;
- wherein the first sheet is held in place by a force exerted by the first and second plates when the apparatus is in an assembled configuration.

10. An apparatus for use in performing a plurality of tests in parallel, the apparatus comprising:
- a first plate having openings extending at least partially therethrough to form a plurality of individual fluid chambers for performing a plurality of tests in parallel;
- a second plate having openings extending at least partially therethrough to form a plurality of fluid cavities, periphery edges of the openings in one of the first and second plates raised relative to a surface of the plate;
- a first sheet having porous test regions interposed between the first and second plates such that a first surface of the first sheet is at least partially exposed to said fluid chambers; and
- a flexible membrane positioned between the first and second plates such that changes in pressure within the fluid chambers or cavities cause deflection of the membrane and force fluid to pass through the porous test regions, the flexible membrane configured to prevent transfer of fluid between said plurality of fluid chambers and said plurality of cavities.

11. The apparatus of claim 10 wherein the test regions are separated by a seal integral with the first sheet and aligned with the fluid chambers such that each of the test regions is exposed to one of said fluid chambers.

12. The apparatus of claim 10 wherein at least one of the plates includes a pressure inlet for receiving pressure and a plurality of passages in communication with the pressure inlet and said fluid chambers.

13. The apparatus of claim 10 wherein the at least one of the plates includes an inlet for receiving pressure or vacuum and a plurality of passages in communication with the inlet and said cavities.

14. An apparatus for use in performing a plurality of tests in parallel, the apparatus comprising:
- a first plate having openings extending at least partially therethrough to form a plurality of fluid chambers;
- a second plate having openings extending at least partially therethrough to form a plurality of cavities;
- a first sheet having porous test regions interposed between the first and second plates such that a first surface of the first sheet is at least partially exposed to said fluid chambers;
- a second sheet having dyed porous test regions interposed between the first and second plates; and
- a flexible membrane positioned between the first and second plates such that changes in pressure within the fluid chambers or cavities cause deflection of the membrane and force fluid to pass through the porous test regions.

15. The apparatus of claim 14 wherein the first and second sheets are positioned immediately adjacent one another.

16. An apparatus for use in performing a plurality of tests in parallel, the apparatus comprising:
- a first plate having openings extending at least partially therethrough to form a plurality of cavities;
- a second plate having a plurality of openings extending at least partially therethrough and forming a plurality of individual fluid chambers for performing a plurality of tests in parallel;
- a first sheet interposed between the first and second plates and having a plurality of porous test regions, the test regions being aligned with the fluid chambers such that each of the test regions is exposed to one of the chambers; and
- a liquid impermeable flexible membrane positioned between the first and second plates such that changes in pressure within the cavities cause deflection of the membrane and force fluid to pass through the porous test regions.

17. The apparatus of claim 16 further comprising a sealing sheet having openings aligned with the test regions and positioned adjacent thereto.

18. The apparatus of claim 16 wherein said fluid chambers each have a fluid volume of between approximately 0.1 milliliters and 5 milliliters.

19. The apparatus of claim 16 wherein said plurality of porous test regions comprise a woven fabric.

20. The apparatus of claim 19 wherein the woven fabric is formed at least partially from cotton.

21. The apparatus of claim 16 wherein said plurality of porous test regions are separated by a seal integral with the first sheet.

22. The apparatus of claim 21 wherein the seal is formed from an ink material.

23. The apparatus of claim 21 wherein the ink material is heat transfer printed on the first sheet.

24. The apparatus of claim 21 wherein the ink material is silk screen printed on the first sheet.

25. An apparatus for use in performing a plurality of tests in parallel, the apparatus comprising:

a first plate;

a second plate having a plurality of openings extending at least partially therethrough and forming a plurality of individual fluid chambers for performing a plurality of tests in parallel;

a first sheet interposed between the first and second plates and having a plurality of porous test regions separated by a seal integral with the first sheet to prevent fluid transfer between the test regions, the test regions being aligned with the fluid chambers such that each of the test regions is exposed to one of the chambers; and a second sheet having dyed porous test regions interposed between the first and second plates;

wherein the first sheet is held in place by a force exerted by the first and second plates when the apparatus is in an assembled configuration and removable from the first and second plates when the apparatus is in an unassembled configuration.

26. The apparatus of claim 25 wherein at least one of the plates includes a pressure inlet for receiving pressure and a plurality of passages in communication with the pressure inlet and said fluid chambers.

* * * * *